(12) United States Patent
Moehring et al.

(10) Patent No.: US 11,850,091 B2
(45) Date of Patent: Dec. 26, 2023

(54) SMALL-SCALE CAPACITIVE ULTRASOUND TRANSDUCER DEVICES AND METHODS

(71) Applicant: OtoNexus Medical Technologies, Inc., Bellevue, WA (US)

(72) Inventors: Mark A. Moehring, Seattle, WA (US); Daniel Kreindler, Foster City, CA (US); George A. Gates, Boerne, TX (US); Caitlin E. Cameron, Mercer Island, WA (US)

(73) Assignee: OtoNexus Medical Technologies, Inc., Bellevue, WA (US)

( * ) Notice: Subject to any disclaimer, the term of this patent is extended or adjusted under 35 U.S.C. 154(b) by 676 days.

(21) Appl. No.: 17/004,568

(22) Filed: Aug. 27, 2020

(65) Prior Publication Data

US 2021/0145406 A1    May 20, 2021

Related U.S. Application Data

(60) Provisional application No. 62/892,930, filed on Aug. 28, 2019.

(51) Int. Cl.
*A61B 8/12*   (2006.01)
*A61B 8/00*   (2006.01)
(Continued)

(52) U.S. Cl.
CPC .............. *A61B 8/4281* (2013.01); *A61B 8/12* (2013.01); *A61B 8/445* (2013.01); *B06B 1/0292* (2013.01);
(Continued)

(58) Field of Classification Search
CPC ......... A61B 8/4281; A61B 8/12; A61B 8/445; A61B 8/565; A61B 8/4444; A61B 8/4483;
(Continued)

(56) References Cited

U.S. PATENT DOCUMENTS 6,775,388 B1    8/2004  Pompei
7,545,075 B2    6/2009  Huang et al.
(Continued)

OTHER PUBLICATIONS

PCT/US20/48288 International Search Report & Written Opinion dated Jan. 19, 2021.
(Continued)

*Primary Examiner* — Emily P Pham
(74) *Attorney, Agent, or Firm* — Wilson Sonsini Goodrich & Rosati

(57) ABSTRACT

An ultrasound transducer may include: a plurality of capacitive ultrasound transducer elements; and a base having a largest dimension sized and shaped to be disposed with an external ear canal, wherein the plurality of capacitive ultrasound transducers is mounted on the base. Each capacitive ultrasound transducer element and the ultrasound transducer are specifically constructed to achieve select desired performance characteristics. The ultrasound transducer may have an angular beam spread through a gaseous medium of greater than 15 degrees and an attenuation loss through the gaseous medium of greater than 10 dB measured at a distance 12.5 mm to 25 mm along a primary transmission axis of the ultrasound transducer. The ultrasound transducer may be particularly useful for characterizing fluid behind an ear drum to diagnose otitis media.

24 Claims, 23 Drawing Sheets

(51) Int. Cl.
  *B06B 1/02* (2006.01)
  *G01N 29/02* (2006.01)
  *G01N 29/24* (2006.01)
  *G01N 29/28* (2006.01)
(52) U.S. Cl.
  CPC .......... *G01N 29/02* (2013.01); *G01N 29/2406* (2013.01); *G01N 29/28* (2013.01); *B06B 1/0207* (2013.01); *B06B 2201/76* (2013.01)
(58) Field of Classification Search
  CPC ........... A61B 8/485; A61B 8/488; A61B 8/10; A61B 8/462; A61B 5/6817; A61B 1/227; B06B 1/0292; B06B 1/0207; B06B 2201/76; G01N 29/02; G01N 29/2406; G01N 29/28; G01S 7/52025; G01S 7/52042; G01S 7/52079; G01S 15/8909
  See application file for complete search history.

(56) References Cited

U.S. PATENT DOCUMENTS

| | | | |
|---|---|---|---|
| 8,079,263 B2 | 12/2011 | Randall et al. | |
| 8,531,919 B2 | 9/2013 | Cheng et al. | |
| 9,925,561 B2 | 3/2018 | Emadi et al. | |
| 2007/0129632 A1* | 6/2007 | Voie | A61B 8/4483 600/438 |
| 2010/0173437 A1 | 7/2010 | Wygant et al. | |
| 2012/0068571 A1 | 3/2012 | Chen | |
| 2014/0265720 A1 | 9/2014 | El-Gamal et al. | |
| 2017/0014053 A1 | 1/2017 | Moehring et al. | |
| 2017/0232474 A1 | 8/2017 | Oralkan et al. | |
| 2017/0289722 A1 | 10/2017 | Ochiai et al. | |
| 2018/0071775 A1 | 3/2018 | Zhuang et al. | |
| 2018/0310917 A1 | 11/2018 | Moehring et al. | |

OTHER PUBLICATIONS

EP20856609.1 Extended European Search Report dated Aug. 17, 2023.

McIntosh et al. Modelling of the radiated field from multi-element capacitive micromachined ultrasonic transducers. Ultrasonics 42 (2004) 447-452.

Tawfik et al. Reduced-gap CMUT implementation in PolyMUMPs for air-coupled and underwater applications. Sensors and Actuators A: Physical: 294 (2019): 102-115.

* cited by examiner

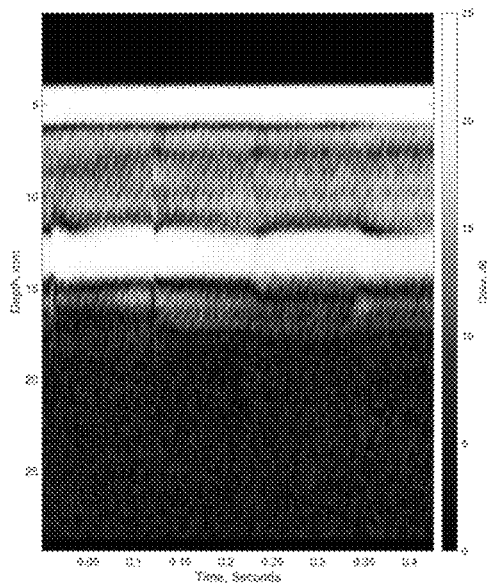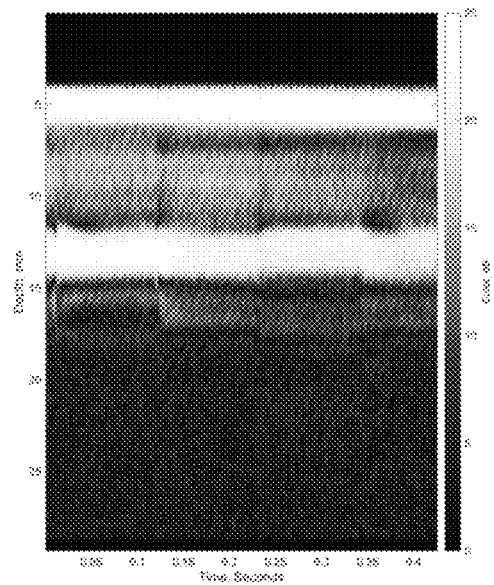
FIG. 8A　　　　　　　　　　FIG. 8B
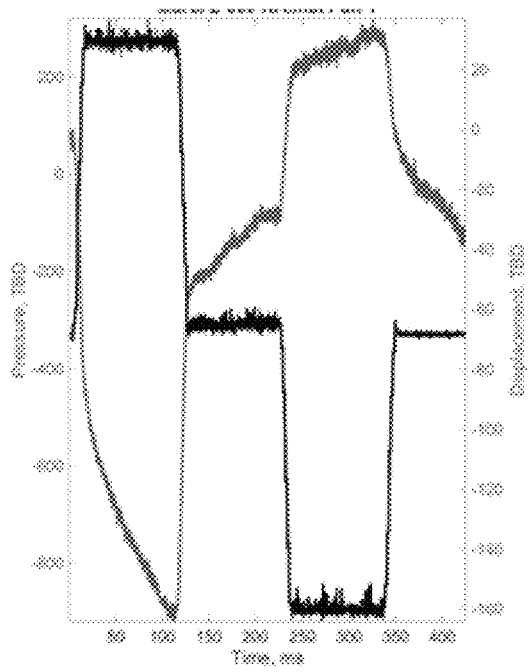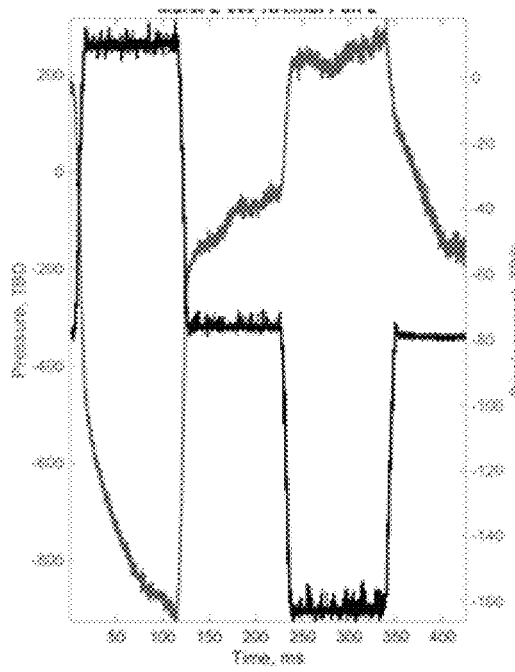
FIG. 9A　　　　　　　　　　FIG. 9B

|  | 50μm | 60μm | 70μm |
|---|---|---|---|
| 6 hole configuration | 4228 | 5228 | 6228 |
| Hole diameter Ø | 42μm | 52μm | 62μm |
| 12 hole configuration | 422 | 522 | 622 |
| Hole diameter Ø | 42μm | 52μm | 62μm |
| Slit configuration | 084 | 084 | 084 |
| Slit-width | 0.8μm | 0.8μm | 0.8μ |
| Spring length | 4μm | 4μm | 4μm |

FIG. 11A

| | 50μm | 60μm | 70μm |
|---|---|---|---|
| Design | 162 | 162 | 162 |
| Hole diameter Ø | 16μm | 16μm | 16μm |
| Design | 302 | 342 | 422 |
| Hole diameter Ø | 30μm | 34μm | 42μm |
| Design | 422 | 522 | 622 |
| Hole diameter Ø | 42μm | 52μm | 62μm |
| Design | 084 | 084 | 084 |
| Slit-width | 0.8μm | 0.8μm | 0.8μm |
| Spring length | 4μm | 4μm | 4μm |
| Design | 088 | 088 | 088 |
| Slit-width | 0.8μm | 0.8μm | 0.8μm |
| Spring-length | 8μm | 8μm | 8μm |

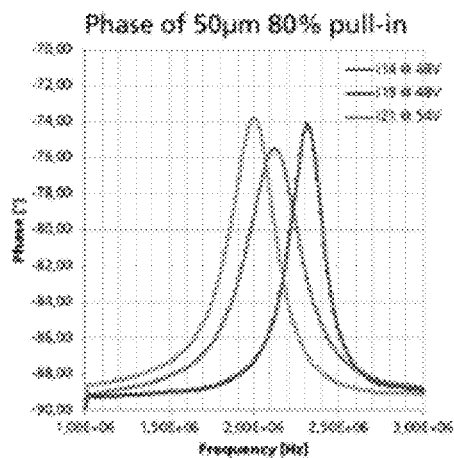 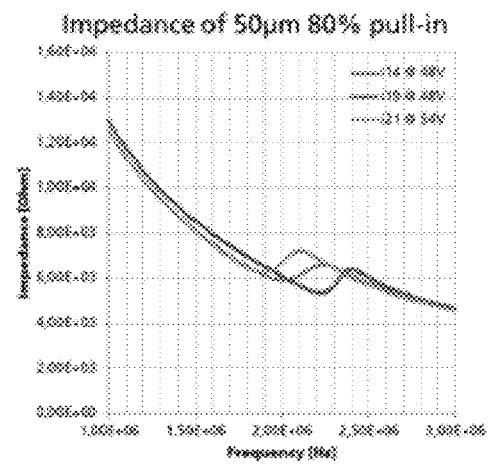
FIG. 14A  FIG. 14B
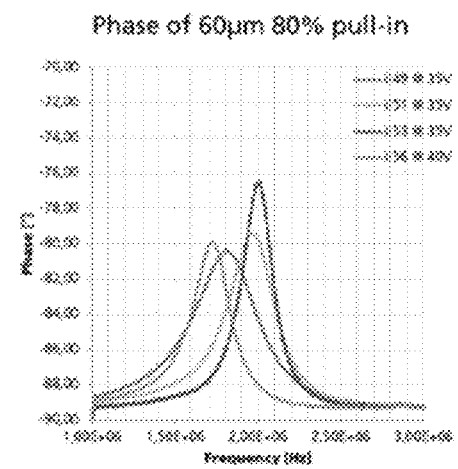 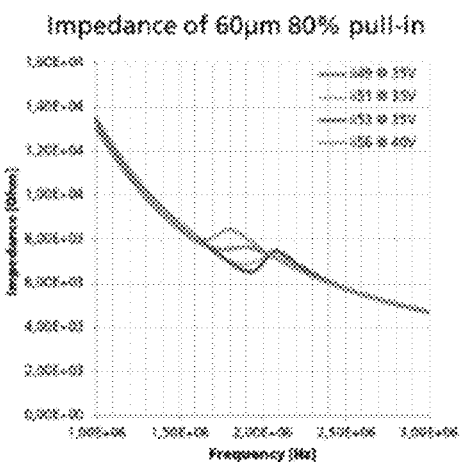
FIG. 14C  FIG. 14D
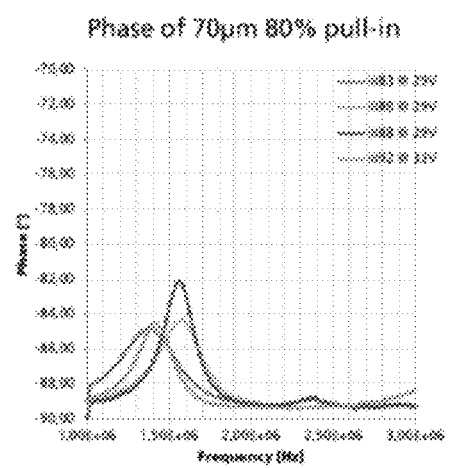 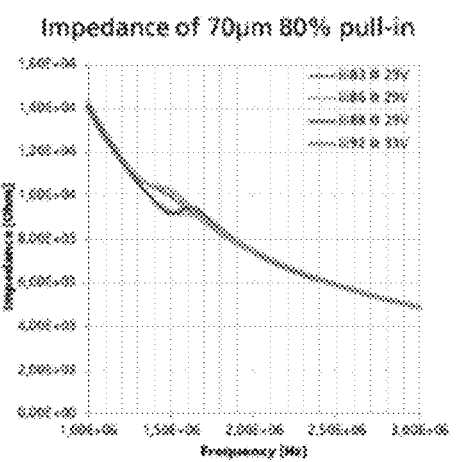
FIG. 14E  FIG. 14F

SMALL-SCALE CAPACITIVE ULTRASOUND TRANSDUCER DEVICES AND METHODS

CROSS-REFERENCE

This application claims the benefit of U.S. Provisional Application No. 62/892,930, filed Aug. 28, 2019, which application is incorporated herein by reference.

BACKGROUND

Determination of an elasticity of a membrane or a viscosity of a fluid may be of interest to a variety of fields including medical diagnosis, medical imaging, manufacturing quality control, food product characterization, industrial process analysis, etc. In many of these applications, it may be beneficial to measure a reflected ultrasound signal using an air-coupled transducer which is small in size. However, small size may pose significant challenges for transducer performance.

In an example, it may be beneficial to characterize a fluid adjacent a biological membrane. Physical access to the biological membrane may be limited. Additionally, coupling gels may not be feasible to use on certain biological membranes. In light of the above, improved systems, devices, and methods for small format air-coupled ultrasound devices are desired.

The present application may be related to commonly owned U.S. Patent Publication 2018/0310917 and U.S. Patent Publication 2017/0014053, each of which is incorporated by reference in their entireties.

The following references may be of interest: U.S. Pat. Nos. 7,545,075, 8,531,919, 9,925,561, 9,925,561, 7,545,075, U.S. Patent Publication 2014/0265720, U.S. Patent Publication 2010/0173437, U.S. Patent Publication 2014/0265720, and U.S. Patent Publication 2012/0068571, each of which is incorporated by reference in their entireties.

SUMMARY

Conventional ultrasound transducers may need to be used with a coupling fluid to match an impedance of a material to be characterized to an ultrasound transducer because the typical medium between the material and the transducer, such as air, may have an acoustic impendence with significant mis-match to a transducer and/or a material to be measured. Transducer devices which are air-coupled may therefore be desired for certain applications. In an example, it may be desirable to use air-couple ultrasound to characterize a fluid on the opposite side of a tympanic membrane of an ear, rather than filling an ear canal with ultrasound gel. Similarly, in this example, it may simultaneously be desirous to make a device small in order to decrease scattering of the ultrasound with air and loss of coherence. One more of sufficient intensity, spatial coherence, small divergence, and/or phase stability, which may be difficult to obtain for air-coupled transducer devices and systems, may be additionally affected by making a transducer device smaller.

The present disclosure provides ultrasound transducer elements, ultrasound transducers, and systems and methods of use and manufacture thereof.

Disclosed herein is an ultrasound transducer comprising a plurality of capacitive ultrasound transducer elements; and a base having a largest dimension sized and shaped to be disposed within an external ear canal, wherein the plurality of capacitive ultrasound transducers is mounted on the base; wherein the ultrasound transducer has an angular beam spread through a gaseous medium of greater than 15 degrees and an attenuation loss through the gaseous medium of greater than 10 dB measured at a distance 12.5 mm to 25 mm along a primary transmission axis of the ultrasound transducer. The largest dimension of the base can be less than 3 mm. The plurality of capacitive ultrasound transducer elements can have a resonant frequency between 1.0 MHz and 3.0 MHz. Each capacitive ultrasound transducer element can have a working surface with a diameter between 10 and 100 microns. The ultrasound transducer can have an edge length of less than 1.5 mm. The plurality of capacitive ultrasound transducer elements can comprise at least 20 capacitive ultrasound transducer elements. The plurality of ultrasound transducers can have an average capacitance between 2.5 pF and 10.0 pF. The ultrasound transducer can be configured to be disposed within a speculum of an otoscope. The one or more of the plurality of capacitive ultrasound transducer elements can have a plurality of openings in a working surface of one or more of the transducer elements. The plurality of openings can be arranged in a circle with a diameter of at least 10 microns. The plurality of openings can comprise at least three release holes per capacitive ultrasound transducer element. The plurality of openings can be circular in shape. The plurality of openings can be curved in shape. The plurality of openings can comprise release slits with a slit-width of a least 0.4 microns and a spring length of a least 2 microns. The plurality of ultrasound transducer elements can be arranged on the base with a hexagonal closest packing structure. The plurality of ultrasound transducer elements can be arranged on the base within a circular area with a diameter equal to the edge length. The plurality of ultrasound transducer elements can be arranged on the base within a rectangular area with a longest side equal to the edge length.

The ultrasound transducer can further comprise a plurality of pads, the pads forming a plurality of electrical contact points. The plurality of capacitive ultrasound transducer elements can have an average cavity height of less than 1500 nm. The ultrasound transducer can have an 80% pull in voltage of less than 85 V. The ultrasound transducer can have a signal to noise ratio greater than 15 dB measured at a distance 12.5 mm to 25 mm along a primary transmission axis of the transducer. The ultrasound transducer can have a fractional bandwidth that exceeds 10%. The ultrasound transducer can have a projected intensity of about 10 Pa or more measured at a distance 12.5 mm to 25 mm along a primary transmission axis of the transducer. The ultrasound transducer can have a frequency bandwidth of plus or minus 25% of center frequency at full width at half maximum.

Disclosed herein is an ultrasound transducer comprising a plurality of capacitive ultrasound transducer elements; and a base having a largest dimension sized and shaped to be disposed with an external ear canal, wherein the plurality of ultrasound transducer elements is mounted on the base; wherein the ultrasound transducer has a fractional bandwidth that exceeds 10%, a projected intensity of about 10 Pa or more, and a signal to noise ratio greater than 15 dB measured at a distance 12.5 mm to 25 mm normal along a primary transmission axis of the ultrasound transducer. The plurality of capacitive ultrasound transducer elements can have a resonant frequency between 1.0 MHz and 3.0 MHz. The ultrasound transducer can have an average capacitance between 2.5 pF and 10.0 pF. The ultrasound transducer can have a pull-in voltage less than 85 V. The ultrasound transducer can have an edge length of less than 1.5 mm. The ultrasound transducer can have an angular beam spread through a gaseous medium of less than 30 degrees and an attenuation loss through the gaseous medium of less than 45 dB measured at a distance 12.5 mm to 25 mm normal to a working surface of the transducer elements. The plurality of capacitive ultrasound transducer elements can comprise at least 20 capacitive ultrasound transducer elements. Each capacitive ultrasound transducer element can have a device radius between 30 microns and 100 microns. The ultrasound transducer can be configured to be disposed within a speculum of an otoscope. One or more of the plurality of capacitive ultrasound transducer elements can have a plurality of openings in a working surface of the one or more of the transducer elements. The plurality of openings can be arranged in a circle with a diameter of greater than 5 microns. The plurality of openings can comprise at least three release holes per capacitive ultrasound transducer element. The plurality of openings can be circular in shape. The plurality of openings can be curved in shape. The plurality of openings can have release slits with a slit-width of a least 0.4 microns and a spring length of a least 2 microns. The plurality of ultrasound transducer elements can be arranged with a hexagonal closest packing structure. The plurality of ultrasound transducer elements can be arranged within a circular area with a diameter equal to the edge length. The plurality of ultrasound transducer elements can be arranged within a rectangular area with a longest side equal to the edge length. The ultrasound transducer can further comprise a plurality of pads, the pads forming a plurality of electrical contact points. The plurality of capacitive ultrasound transducer elements can have an average cavity height of less than 1500 nm. The ultrasound transducer can have an 80% pull in voltage of less than 85 V. The ultrasound transducer can have a frequency bandwidth of plus or minus 25% of center frequency at full width at half maximum. Disclosed herein is a system comprising the capacitive ultrasound transducer of any of claims 1 to 46 and a speculum, wherein the capacitive ultrasound transducer is disposed with the speculum and wherein the speculum is configured to be removably coupled an otoscope. Disclosed herein is a method of measuring a fluid, the method comprising providing the capacitive ultrasound transducer of any of claims 1 to 46; applying a pneumatic challenge to a surface of the fluid; and observing with the capacitive ultrasound transducer a perturbation in a waveform reflected from the surface in response to the pneumatic challenge. Disclosed herein is a method of characterizing a fluid, the method comprising providing an ultrasound transducer; and directing an ultrasound beam generated by the ultrasound transducer toward a surface of the fluid through a gaseous medium, wherein the fluid is a distance of 12.5 mm to 25 mm from a working surface of the ultrasound transducer, wherein the ultrasound beam has an angular beam spread through the gaseous medium of greater than 15 degrees, and wherein the ultrasound beam has an attenuation loss through the gaseous medium of greater than 10 dB. Disclosed herein is a method of characterizing a fluid behind an ear drum in an ear canal, the method comprising receiving a set of data from an ultrasound transducer, wherein the ultrasound transducer is disposed within the ear canal of a subject, wherein the ultrasound transducer has an edge length of less than 1.5 mm; determining from the set of data a first subset of data corresponding to a response to a pneumatic challenge and a second subset of data corresponding to an unchallenged data set; determining a viscosity of the fluid; and classifying the fluid.

Disclosed herein is an otoscope comprising a disposable speculum; a plurality of capacitive ultrasound transducers disposed within the speculum, wherein the plurality of ultrasound transducer elements form an ultrasound transducer, wherein the ultrasound transducer is disposed within the speculum tip, and wherein the ultrasound transducer has an angular beam spread through a gaseous medium of greater than 15 degrees and an attenuation loss through the gaseous medium of greater than 10 dB measured at a distance 12.5 mm to 25 mm along a primary transmission axis of the transducer; and a base, wherein the base comprises a largest dimension of less than 2.5 mm, wherein the plurality of capacitive ultrasound transducers is disposed on the base.

Disclosed herein is a method of manufacturing a fluid measuring device, the method comprising forming a plurality of capacitive ultrasound transducer elements on a wafer surface, having a device radius between 10 microns and 100 microns, wherein the plurality of ultrasound transducer elements are arranged in a hexagonal closest packing structure, wherein one or more of the plurality of ultrasound transducer elements comprise a plurality of openings in a working surface of the one or more of the transducer elements, wherein the plurality of openings comprises between 4 and 20 openings; cutting the wafer into a plurality of individual capacitive ultrasound transducers; and mounting a single ultrasound transducer within a speculum of an otoscope. The method can further comprise removably coupling the speculum to the otoscope.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 8A and FIG. 8B show example data traces showing false color contour plots of membrane motion in response to a perturbation, in accordance with some embodiments.

FIG. 9A and FIG. 9B show example pressure and displacement versus time curves, which correspond to the perturbation applied in the examples of FIG. 8A and FIG. 8B, respectively, in accordance with some embodiments.

FIG. 11A and FIG. 11B show top view schematics of example working surface designs for transducer elements as tested, in accordance with some embodiments.

FIG. 12A and FIG. 12B show tables of the layout of tested example ultrasound transducer configurations, in accordance with some embodiments.

FIG. 14A, FIG. 14B, FIG. 14C, FIG. 14D, FIG. 14E, and FIG. 14F show plots of phase and impedance versus frequency for various ultrasound transducers tested, in accordance with some embodiments.

DETAILED DESCRIPTION

Figure 1A:
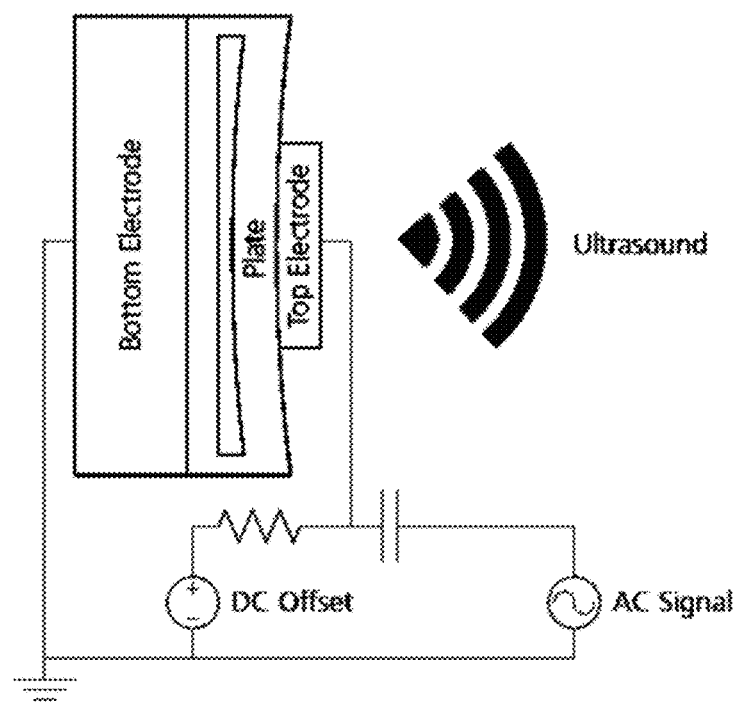
FIG. 1A illustrates a schematic of an ultrasound transducer element in a transmit mode, in accordance with some embodiments.

Embodiments of the present disclosure provide ultrasound transducers. An example ultrasound transducer may comprise a plurality of capacitive ultrasound transducer elements, and a base, wherein the plurality of capacitive ultrasound transducers is mounted on the base. The capacitive ultrasound transducer elements may be a plurality of capacitive micro-machined ultrasound transducer (cMUT) elements. The cMUTs may form an ultrasound transducer configured to direct ultrasound energy through air.

Each capacitive ultrasound transducer element and the ultrasound transducer may be specifically constructed to achieve select desired performance characteristics. For example, the base may be small. In some cases, the base may have a largest dimension sized and shaped to be disposed with an external ear canal. The plurality of capacitive ultrasound elements comprising a transducer may be mounted on the base. The ultrasound transducer may have an angular spread, of its main lobe within a gaseous medium, of greater than 15 degrees. Further, the emanated ultrasound may have an attenuation loss through the gaseous medium of greater than 10 dB measured at a distance 12.5 mm to 25 mm along a primary transmission axis of the ultrasound transducer. The ultrasound transducer may be particularly useful for characterizing fluid behind an ear drum, to diagnose otitis media.

In some embodiments, the ultrasound transducer measures the dynamic displacement characteristics of the membrane or surface in response to a pneumatic challenge to the membrane or to a surface adjacent the membrane. The ultrasound transducer sends and receives ultrasound energy through a medium such as air to the surface or membrane to be characterized. Accordingly, the ultrasound energy may be sufficiently intense, may comprise a plane wave with spatial extent to match the material to be characterized, and/or may comprise sufficient phase stability across the spatial extent of the planar wave for measurements of the reflected phase to be measured.

Other design considerations may include size. For example, the base may be small. For example, the base may be sufficiently small to be positioned within a body lumen, such as an ear canal. The base may be mounted within a speculum or other delivery device to be disposed within a body lumen. In some examples, the plurality of transducers mounted on the base is sufficiently small to be disposed within an ear canal. In some examples, the base has a largest dimension of less than 10 millimeters (mm), 3 mm, 1 mm, or less. In addition to small size, the ultrasound transducer may be configured to direct an ultrasound beam through a gaseous medium with an appropriate angular beam spread, attenuation, and/or loss of coherence.

In an example, a material may be characterized by the application of a challenge displacement force such as by an air puff concurrent with measurement of a reflected ultrasound signal from the material. The material may be a membrane. The material may be a material beneath a membrane. In some cases, the membrane may transparently provide a physical barrier to the material to be characterized and may not significantly change the properties of a material opposite the membrane as seen by the ultrasound transducer.

The transducers, transducer elements, and methods of use and manufacture thereof may be used in combination with methods to characterize a ductile membrane, surface, and sub-surface properties such as those described in commonly owned U.S. Patent Publication 2018/0310917 and U.S. Patent Publication 2017/0014053, each of which is incorporated by reference in their entireties.

Reference will now be made in detail to various embodiments, examples of which are illustrated in the accompanying drawings. In the following detailed description, numerous specific details are set forth in order to provide a thorough understanding of the invention and the described embodiments. However, the invention is optionally practiced without these specific details. In other instances, well-known methods, procedures, components, and circuits have not been described in detail so as not to unnecessarily obscure aspects of the embodiments.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

Ultrasound Transducer

FIG. 1A illustrates schematic of an ultrasound transducer in a transmit mode, in accordance with some embodiments. In some cases, the ultrasound transducer may be a capacitive micro-machined ultrasound transducer (cMUT). Rather than a piezoelectric transducer, a cMUT may be driven by changes in capacitance between a working surface of the transducer, e.g., a membrane, a plate, etc., and a substrate. A transmit waveform supplied to the transducer element by a digital processing device may be converted to an ultrasound signal by oscillation of the working surface. The working surface may be electrically connected to a first electrode. The substrate may be electrically connected to a second electrode. The transducer element may comprise driving circuitry which may control the capacitance of the transducer element such as by applying a voltage or a current between the first and second electrodes. The applied voltage may comprise a voltage offset from a system ground and a driving signal. The driving signal may comprise a voltage that varies with time according to a driving waveform. The driving waveform may be the analog output from a digital-to-analog converter in response to a digital signal from a digital processing device as described elsewhere herein. The driving circuitry may comprise additional components not shown, such as amplifiers, filters, mixers, etc. These additional components may be themselves analog or digital elements. In some embodiments, a digital component such as a digital amplifier, digital filter, or digital mixer may be implemented by a digital processing device as described herein.

Figure 1B:
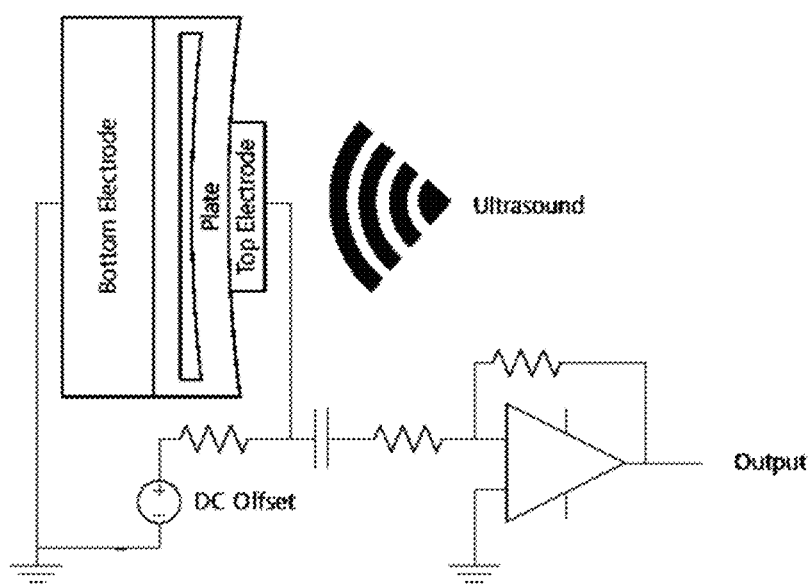
FIG. 1B illustrates a schematic of an ultrasound transducer element in a receive mode, in accordance with some embodiments.

FIG. 1B illustrates a schematic of an ultrasound transducer in a receive mode, in accordance with some embodiments. In some embodiments, the illustrated embodiment of FIG. 1B is the same ultrasound transducer of FIG. 1A. In other embodiments, individual transducer elements may be configured specifically as receiving elements and transmitting elements. The ultrasound transducer of FIG. 1B may comprise similar elements to the transducer of FIG. 1A. For example, the ultrasound transducer may be a capacitive micro-machined ultrasound transducer (cMUT). The transducer may be driven by changes in capacitance between a working surface of the transducer, e.g. a membrane, a plate, etc., and a substrate. A received ultrasound signal may be detected by the transducer element and supplied to a digital processing device. The received signal may be converted to an electrical signal by oscillation of the working surface, which changes the capacitance of the transducer element. The working surface may be electrically connected to a first electrode. The substrate may be electrically connected to a second electrode. The transducer element may comprise driving circuitry which may detect the change in capacitance of the transducer element such as by detecting a change in a voltage or a current between the first and second electrodes. The varying voltage or current may directed an analog-to-digital converter to create a digital signal which may be received by a digital processing device as described elsewhere herein. The driving circuitry may comprise additional components not shown, such as amplifiers, filters, mixers, etc. These additional components may be themselves analog or digital elements. In some embodiments, a digital component such as a digital amplifier, digital filter, or digital mixer may be implemented by a digital processing device as described herein.

Figure 2A:
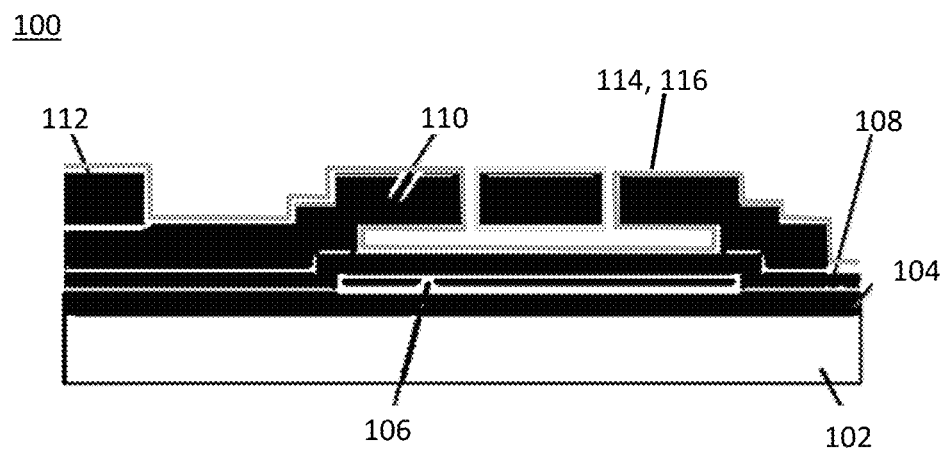
FIG. 2A illustrates a section view of a transducer element of an ultrasound transducer, in accordance with some embodiments.

FIG. 2A illustrates a section view of a transducer element of a cMUT, in accordance with some embodiments. The illustrated embodiment may be an embodiment, variation, or example of the transducer element in FIG. 1A or FIG. 1B. As shown the transducer element 100 may comprise a substrate 102, a first isolation layer 104, a bottom electrode 106, a second isolation layer 108, a plate layer or top electrode 110, a pad contact 112, an oxide layer 114, and a hydrophobic protective layer 116.

In some cases, the substrate may be silicon, gallium nitride, silicon carbide, etc. The substrate may be single crystal or amorphous. The substrate may be single side polished silicon. The substrate may be double sided polished silicon. The substrate may be a glass. The substrate may be provided with a range of thicknesses. The substrate may have a thickness within a range between 200 microns and 5000 microns. The substrate may have a thickness within a range between 650 microns and 700 microns. The substrate may be about 675 microns in thickness. The substrate may be a portion of a wafer or carrier. The substrate may be a portion of a base.

The substrate may be electrically isolated from the driving circuitry or a working surface of the transducer element. The substrate may be electrically isolated by a first isolation layer. The first isolation layer may comprise silicon dioxide. The first isolation layer may be provided with a range of thicknesses. The first isolation layer may have a thickness within a range from 990 to 1100 nanometers (nm) in thickness. The first isolation layer may be about 1000 nm in thickness.

The transducer element may comprise a bottom electrode. The bottom electrode may be electrically conducting. The bottom electrode may comprise titanium and aluminum. The bottom electrode may comprise TiAl or similar materials. The bottom electrode may be provided with a range of thicknesses. The bottom electrode may have a thickness within a range between 180 and 220 nm. The bottom electrode may have a thickness of about 200 nm. The bottom electrode may be electrically isolated from a substrate and a working surface of the transducer. The bottom electrode may be electrically connected to driving circuitry by an exposed electrical contact (e.g., a "pad").

The transducer element may comprise a second isolation layer which may isolate a bottom electrode from a working surface of the transducer element. The second isolation layer may additionally isolate a top electrode from a bottom electrode and a substrate. The second isolation layer may comprise silicon dioxide or similar insulating material. The second isolation layer may comprise a plasma enhanced oxide layer. The second isolation layer may be provided with a range of thicknesses. The second isolation layer may have a thickness within a range between 180 and 220 nm. The second isolation layer may have a thickness of about 200 nm.

The transducer element may comprise a plate layer. The plate layer may be electrically conductive. If the plate layer is electrically conductive, the plate layer may be the top electrode. The plate layer may comprise the top electrode. The plate layer may be electrically connected to the top electrode. The plate layer may comprise the working surface of the transducer, which may be referred to as the membrane or plate. The top electrode may be electrically connected to driving circuitry by an electrical contact (e.g., a "pad"). The plate layer may be provided with a range of thicknesses. The plate layer may have a thickness within a range between 450 and 550 nm. The plate layer may have a thickness of about 500 nm. The plate layer may comprise Titanium and Aluminum. The plate layer may me made of TiAl or similar materials.

The plate layer may be temporarily separated from the second isolation layer by a sacrificial layer. The thickness of the sacrificial layer may be related to the height of the cavity between the working surface and the second sacrificial layer. The cavity may be formed with a range of heights. In some cases, the height of the cavity may be greater than about 50 nm, 100 nm, 200 nm, 500 nm, 1000 nm, 2000 nm, or any height within range defined by any two of the preceding values. In some cases, the average cavity height may less than about 1500 nm, less than about 1000 nm, or less. In some cases, the height of the cavity may be about 350 nm, about 850 nm, about 1100 nm.

The exposed surfaces of the cMUT may be coated with a silicon oxide, or other suitable oxide with a thickness of 2 to 100 nanometers (nm). The exposed surfaces of the cMUT can be coated with a silicon dioxide or other suitable oxide with a thickness of greater than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nm. The exposed surfaces of the cMUT can be coated with a silicon dioxide or other suitable oxide with a thickness of less than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30 29, 28, 27, 26, 25, 24, 23, 22, 21, 20, 19, 18, 17, 16, 15, 14, 13, 12, 11, 10, 9, 8, 7, 6, 5, 4, 3, or 2 nm.

The exposed surfaces of the cMUT may be coated with a hydrophobic material, such as polytetrafluoroethylene or perfluorodecyltrichlorosilane with a thickness of 1 to 200 nm. The exposed surfaces of the cMUT can be coated with a hydrophobic material with a thickness of greater than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nm. The exposed surfaces of the cMUT can be coated with a hydrophobic material with a thickness of less than 200, 199, 198, 197, 196, 195, 194, 193, 192, 191, 190, 189, 188, 187, 186, 185, 184, 183, 182, 181, 180, 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30 29, 28, 27, 26, 25, 24, 23, 22, 21, 20, 19, 18, 17, 16, 15, 14, 13, 12, 11, 10, 9, 8, 7, 6, 5, 4, 3, or 2 nm.

Figure 2B:
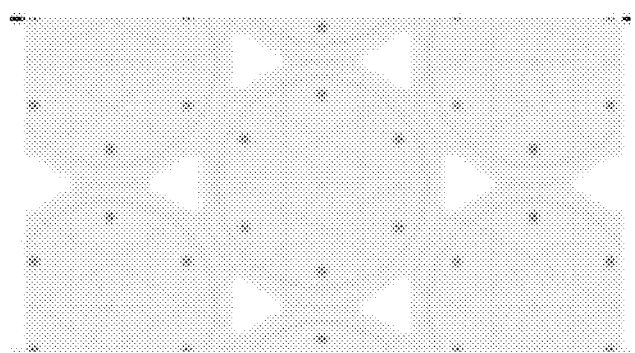
FIG. 2B illustrates a top view of a transducer element of an ultrasound transducer, in accordance with some embodiments.

FIG. 2B illustrates a top view of a transducer element, in accordance with some embodiments. In some cases, the plate layer may comprise a circular working surface. The working surface may be circular to within a 10% variation in a diameter. In some cases, the working surface is a polygon. For example, the working surface may be a hexagon, octagon, decagon, dodecagon, etc. The working surface may be provided with a range of diameters. In some cases, the element has working surface with a diameter between 30 microns and 100 microns. The largest dimension across the working surface of the transducer may be less than about 10 microns, about 20 microns, about 50 microns, 100 microns, about 200 microns, about 500 microns, or within a range defined by any two the preceding values.

The plate layer may comprise one or a plurality of holes or openings within the working surface of the transducer element. The release holes may facilitate movement of the working surface. The release holes may change characteristics of the movement of the workings surface, such as the frequency, operating voltage, operating impedance, operating capacitance, etc. In some cases, the element comprises a plurality of openings in a working surface. In some cases, there may be at least about 2 holes, about 5 holes, about 10 holes, about 20 holes, about 50 holes, about 100 holes, or any number of holes within a range defined by any two of the preceding values. In some cases, there may be at least three release holes per capacitive ultrasound transducer element. In the illustrated embodiment, the transducer element has 6 round holes evenly spaced angularly on a 40 micron circle centered within the working surface of the transducer element.

The holes may be arranged in a regular geometric pattern within the surface of the transducer or may be irregularly spaced. In some cases, the holes are arranged in a circle. In some cases, the openings are arranged in a circle with a diameter of greater than 5 microns. The holes may be evenly spaced angularly in a circle with a diameter less than about 5 microns, 10 microns, 20 microns, 50 microns, 100 microns, 200 microns, or any diameter within a range defined by any two of the preceding values. The holes in the working surface may be round or may be cut as flaps. In some cases, the holes are cut as slits. In some cases, the openings are circular. In some cases, the openings are curved.

A slit shaped opening may have a slit width. A flap may have a slit width and a spring length. A slit width may be less than about 1 micron, about 2 microns, about 5 microns, about 10 microns, about 20 microns, about 50 microns, about 100 microns, or any length within a range defined by any two of the preceding values. A spring length may be less than about 0.2 microns, 0.5 microns, 1 micron, 2 microns, 5 microns, 10 microns, 20 microns or any length within a range defined by any two of the preceding values. In some cases, the openings may be shaped as release slits with a slit-width of a least 0.4 microns and a spring length of a least 2 microns. In some cases, there are no etch holes in the working surface of the device. The size, shape, and placement of holes in the working surface of the transducer element may tune the bandwidth and sensitivity of the transducer element.

Figure 3A:
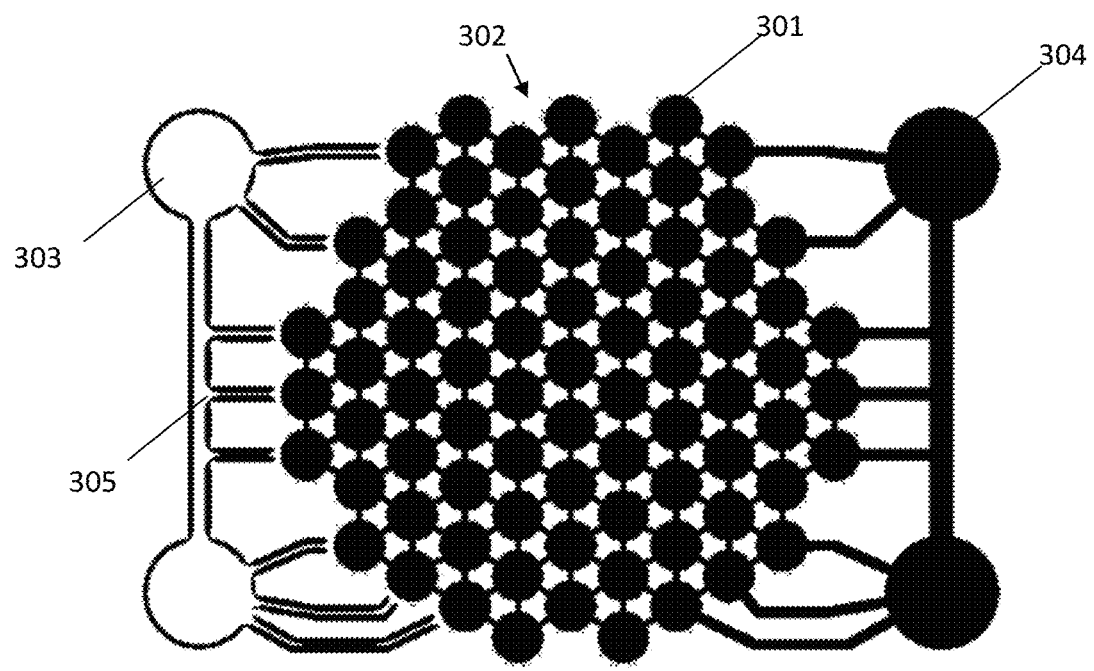
FIG. 3A illustrates a schematic top view of an ultrasound transducer comprising a plurality of transducer elements, in accordance with some embodiments.

FIG. 3A illustrates a schematic top view of an ultrasound transducer comprising a plurality of transducer elements 301, in accordance with some embodiments. A plurality of transducer elements 301 may be arranged together to form an ultrasound transducer 300. The ultrasound transducer 300 may comprise electrical connections, 305, which may provide controllable driving current or voltage to the top 303 and bottom electrodes 304 of each transducer element. The ultrasound transducer may comprise a plurality of pads 303, 304, the pads forming a plurality of electrical contact points. As shown, the top electrode of each transducer element may be electrically connected to one or more top drive pads 303. As shown the bottom electrode of each transducer element may be electrically connected to one or more bottom drive pads 304. The bottom drive pads 304 and the top drive pads 303 respectively may be connected to control circuitry such as a digital-to-analog convert, digital processing device, etc. as discussed elsewhere herein.

The ultrasound transducer may comprise between 10 and 1000 transducer elements. In some cases, the ultrasound transducer comprises between 50 and 200 transducer elements. The ultrasound transducer may comprise more than about 10, about 20, about 50, about 100, about 200, about 500, or more transducer elements. The ultrasound transducer may comprise about 80 transducer elements. In some cases, the ultrasound transducer comprises at least 20 capacitive ultrasound transducer elements.

The plurality of ultrasound transducer elements may be arranged in a pattern to form an ultrasound transducer. The pattern may be a regular pattern. The pattern may be an irregular pattern. The transducer elements may be arranged in a hexagonal close-packed arrangement. The transducer elements may be arranged in a rectangular close-packed arrangement. The transducer elements may be arranged in a non-geometric pattern. The elements of the ultrasound transducer may be arranged within a circular area with a diameter equal to the edge length. The elements of the ultrasound transducer may be arranged within a rectangular area with a longest side equal to the edge length. The ultrasound transducer may have a largest dimension across the surface of the ultrasound transducer. The largest dimension may the furthest distance between the furthest two working edges of the furthest two transducers in the arrangement. The ultrasound transducer may comprise a largest dimension which may be less than about 1 mm, about 2 mm, about 5 mm, etc. The largest dimension may provide a lower threshold on the smallest surface dimension of the base. Accordingly, the largest dimension should be smaller than a diameter of a bodily lumen into which the transducer may be disposed, for example, an ear canal.

The elements of the ultrasound transducer may be electrically connected to one another by way of one or more conductors connecting an element with a second element. In some cases, each top electrode of each element may be connected to each other top electrode of the ultrasound transducer. In some cases, each bottom electrode of each element may be connected to each other bottom electrode of the ultrasound transducer. There may be a single electrical contact for the top electrodes of the ultrasound transducer, and a single electrical contact for the bottom electrodes. There may be two contacts for the commonly wired top electrodes and two contacts for the commonly wired bottom electrodes. In other cases, the elements may be electrically controlled independently or in groups. Each element or group of elements may be controlled by its own contacts. In an example, all transducer elements are commonly controlled with a single driving waveform.

In cases where the top and bottom electrodes are commonly connected, all or most of the elements of the transducer may operate in tandem. For example, when a voltage is applied all or most of the transducer elements may move synchronously. Elements on the outer edge of the transducer may show a phase offset (e.g. may deflect earlier or later than elements in the center of the transducer). In some cases, individual elements may display a phase offset due to irregularities in manufacturing. A transducer whose elements operate more closely to operating in the same phase may show improved performance over a transducer whose elements operate further from the same phase. Similarly, a transducer whose elements operate with more similar amplitude deflection may show improved performance.

Figure 3B:
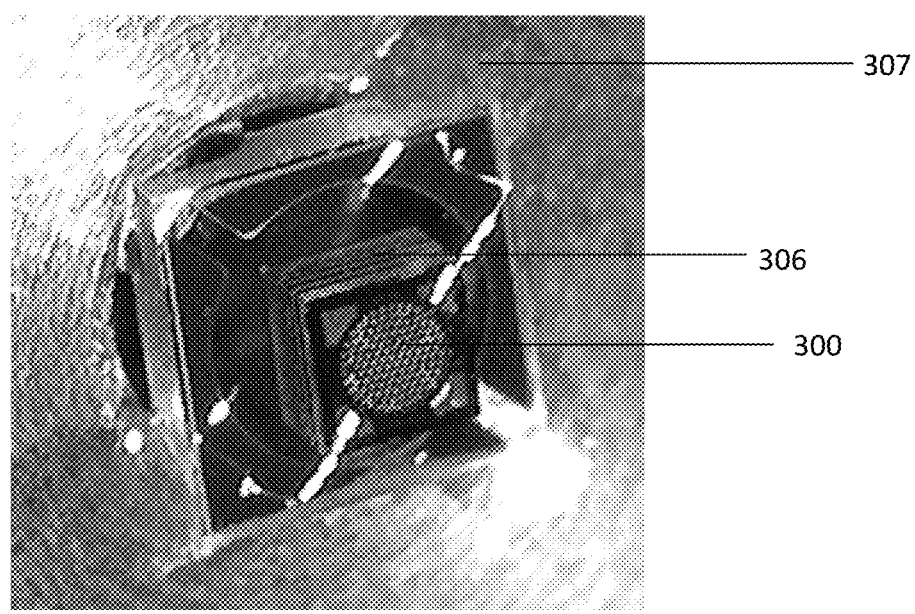
FIG. 3B is an image of an ultrasound transducer on a base, in accordance with some embodiments.

FIG. 3B is an image of an ultrasound transducer 300 on a base 306, in accordance with some embodiments. The base 306 may comprise a substrate described elsewhere herein. In some embodiments, the substrate is disposed on a carriage material, which may be a part of a base. The base 306 may allow for mounting of the ultrasound transducer on a device of the present disclosure. For example, the base 306 may be mounted on a tip of speculum 307 described elsewhere herein. The base 306 may comprise electrical connections such as wiring, VIAs (Vertical Interconnect Access), etc. necessary to conduct electrical signals from the ultrasound transducer to a digital processing device. The base 306 may comprise electrical connections such as wiring, VIAs, etc. necessary to conduct electrical signals to an analog front end, which both drives the ultrasound transducer to produce acoustic output and listens to the ultrasound transducer to capture acoustic echoes from objects/interfaces in the transducer's beam path. The base 306 may protect the ultrasound transducer. The base 306 may stiffen and/or provide additional support to the substrate of the ultrasound transducer. The base 306 may comprise a portion of the wafer upon which an ultrasound transducer was manufactured.

Figure 4A:
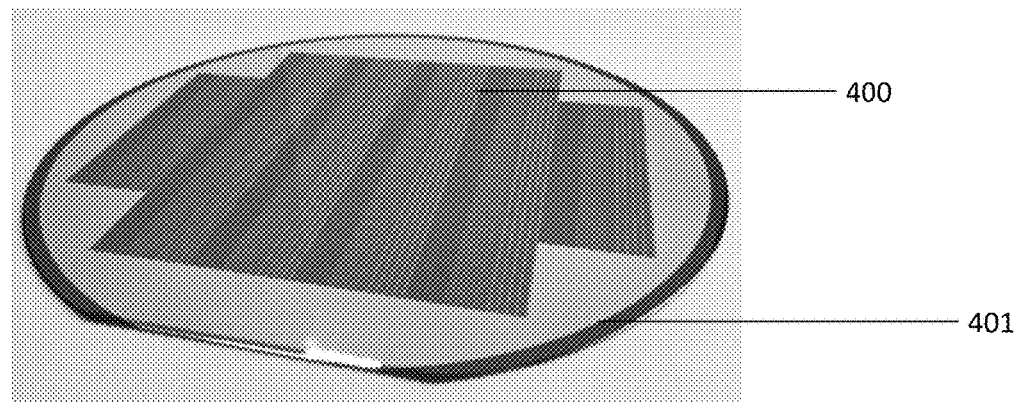
FIG. 4A is an image of a plurality of ultrasound transducers on a wafer, in accordance with some embodiments.
Figure 4B:
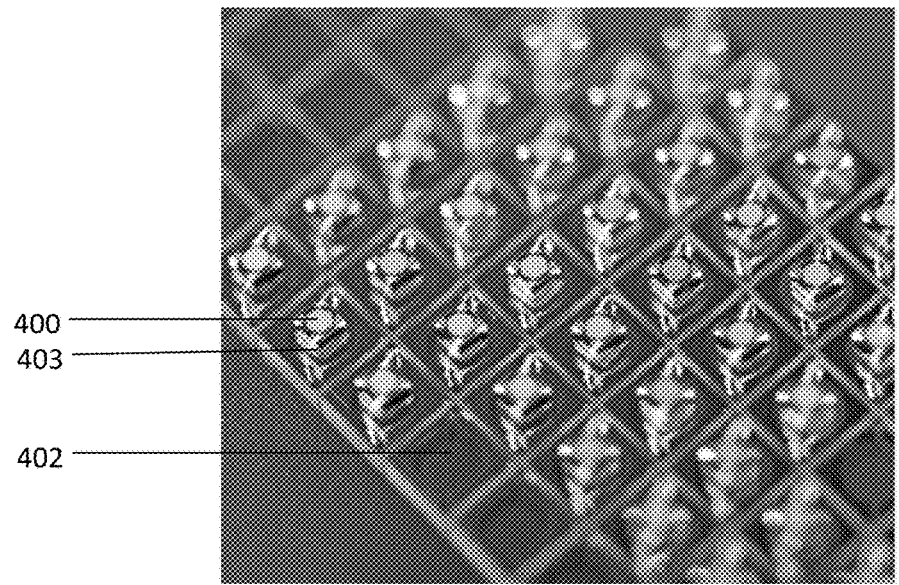
FIG. 4B is an image of a plurality of ultrasound transducers after being separated from a wafer, in accordance with some embodiments.
Figure 5A:
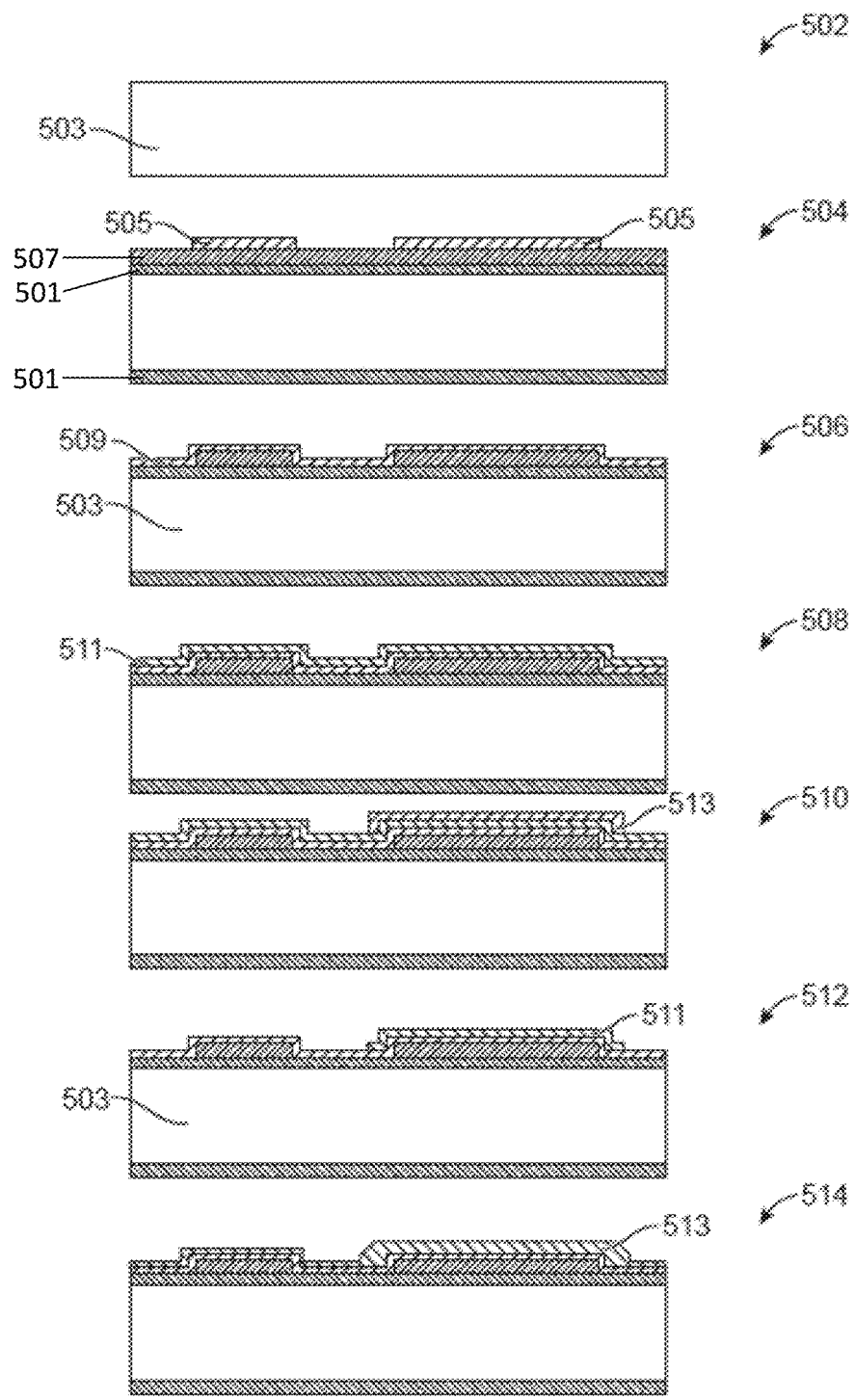
FIG. 5A, FIG. 5B, FIG. 5C, and FIG. 5D illustrate a method of manufacturing a cMUT element, in accordance with some embodiments.
Figure 5B:
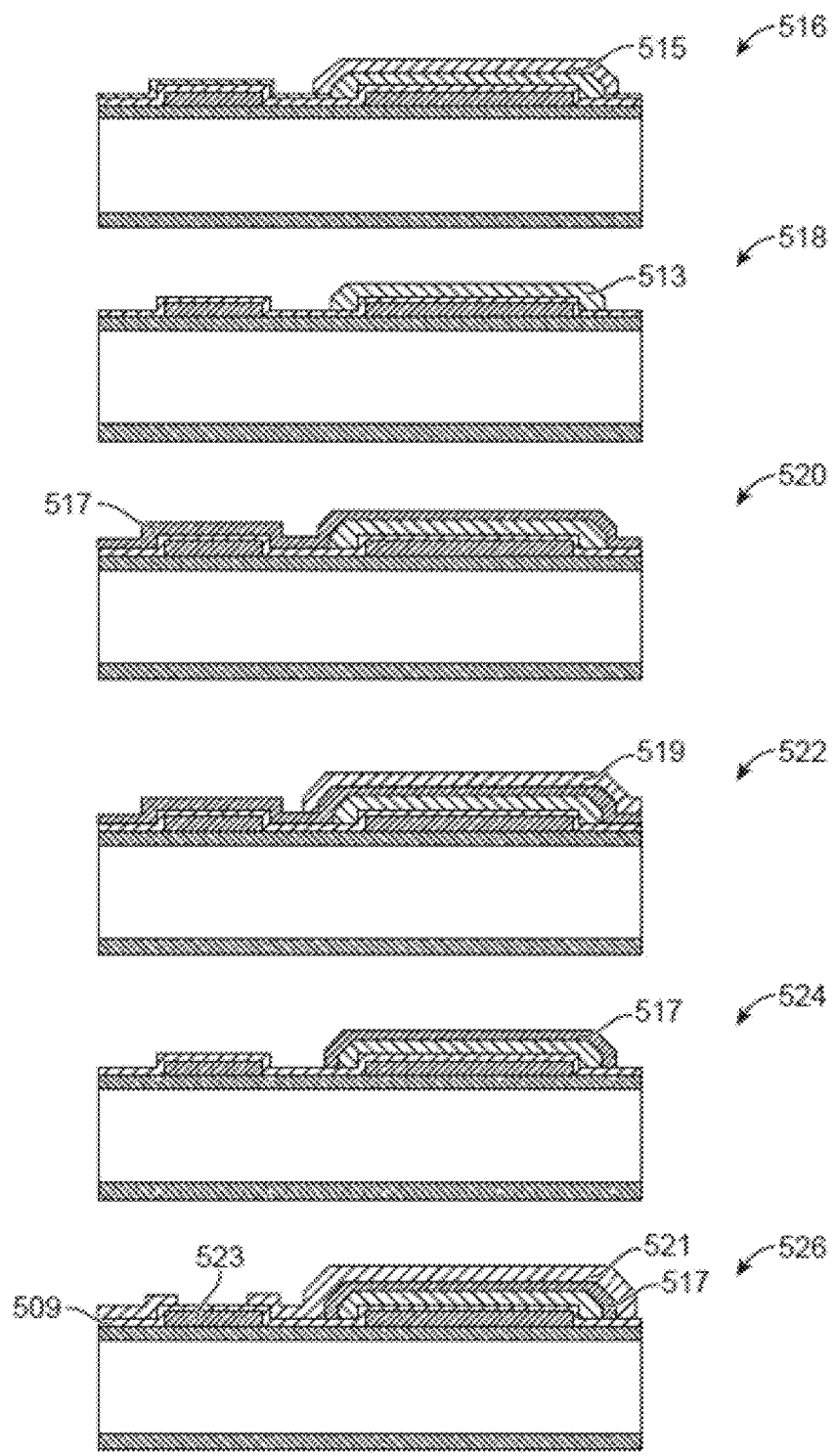
Figure 5C:
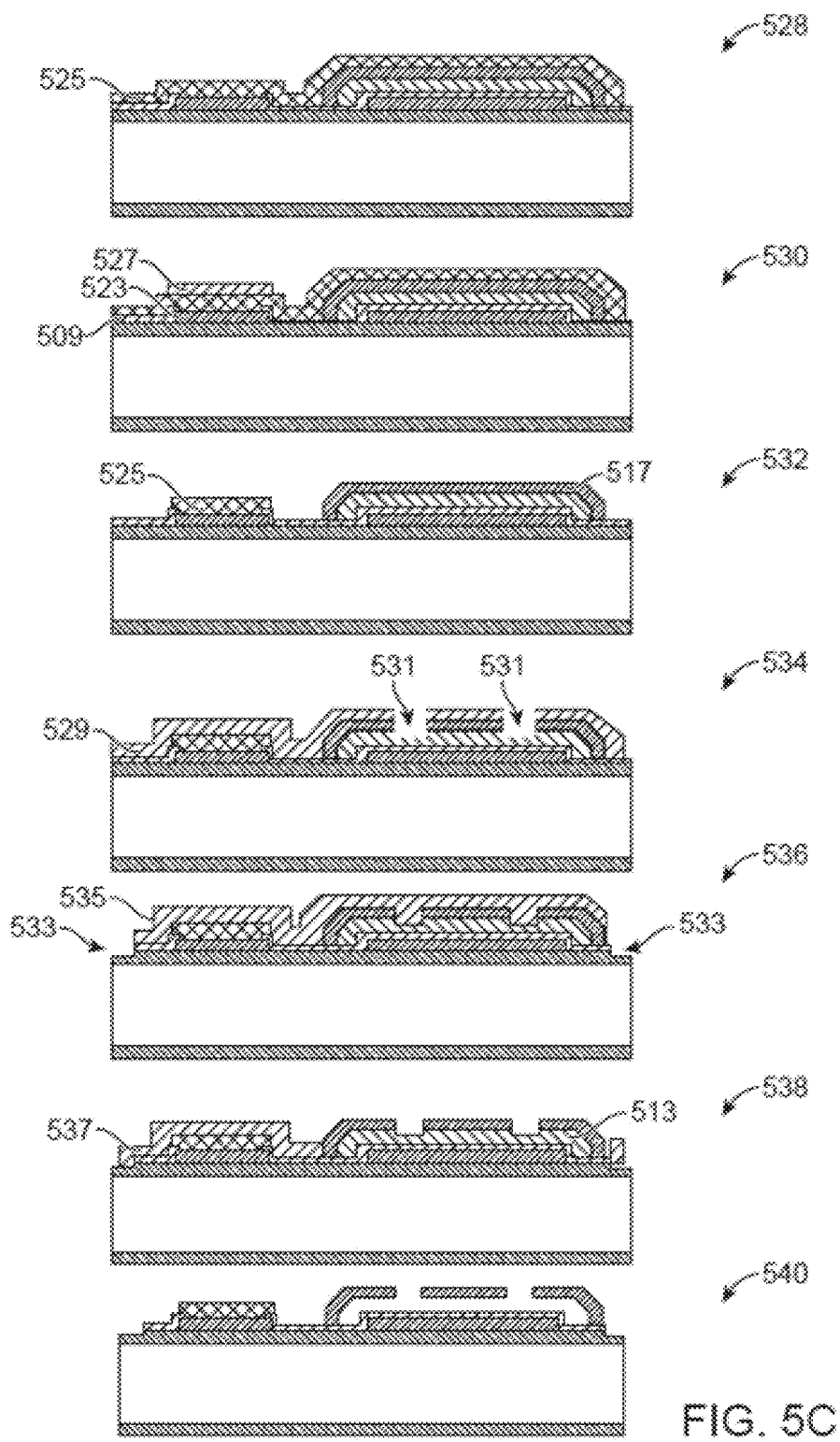
Figure 5D:
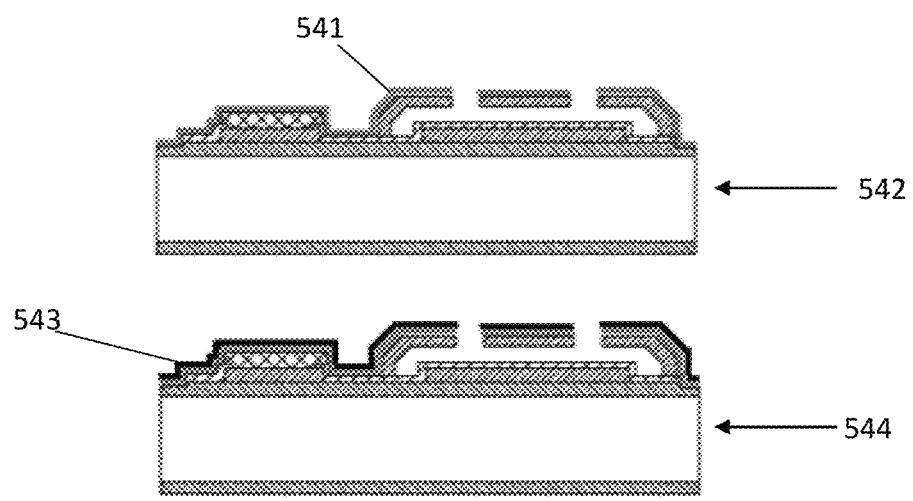

Methods of manufacture of the transducer elements and ultrasound transducers provided are disclosed herein. In some examples, a plurality of ultrasound transducers, each of which comprising a plurality of transducer elements, may be manufactured simultaneously. FIG. 4A is an image of a plurality of cMUTs 400 on a wafer 401, in accordance with some embodiments. The ultrasound transducers may be individually separated from the wafer by cutting (e.g., dicing) the wafer or by a lift off. FIG. 4B is an image of a plurality of cMUTs 400 after being separated from a wafer 401, in accordance with some embodiments. As shown, the plurality of ultrasound transducers may further comprise a portion of the wafer or a sacrificial material disposed on the wafer 402, which may aid in mounting the transducer. All or a portion of the base 403 may be manufactured on the wafer.

FIG. 5A, FIG. 5B, FIG. 5C, and FIG. 5D illustrate a method 500 of manufacturing one or a plurality of cMUT elements, in accordance with some embodiments. At an operation 502, a silicon wafer 503 may be provided. The silicon wafer 503 may be cleaned. The silicon wafer 503 may comprise a substrate as disclosed elsewhere herein. At an operation 504, layers of the first isolation material 501 and the bottom electrode material 507 may each be deposited. A protective plate 505 may be placed over a portion of the bottom electrode material 507. The lithography for the bottom electrode 507 is shown. At an operation 506, the second electrode material may be etched and the second isolation material 509 deposited on the surface. At an operation 508, a first sacrificial layer 511 may be deposited. At an operation 510, the lithography for the sacrificial layer 511 is shown. A protective layer 513 may be placed over a portion of the sacrificial layer. At an operation 512, a portion of the sacrificial layer may be etched thereby starting a structure of the sacrificial layer 511. At an operation 514, a second sacrificial layer 513 may be added to the first. The second layer may thereby form a sloping sidewall. At an operation 516, lithography for the second sacrificial layer is shown. A protective layer 515 may be placed over a portion of the second sacrificial layer. At an operation 518, a portion of the sacrificial layer 513 may be structured via plasma etching. At an operation 520, a plate layer 517 may be deposited. At an operation 522, lithography for the plate layer is shown. A protective layer 519 may be placed over a portion of the plate layer. At an operation 524, a portion of the plate layer may be etched to structure the plate layer 517. At an operation 526, lithography for the plate layer is shown. A protective mask 521 may be placed over the isolation material layer 509 and the plate layer 517. Also shown is etching to open the contact pad 523 by etching the isolation material layer 509. At an operation 528, deposition of the contact pad material 525 may be performed. At an operation 530, lithography for the contact pad 523 is shown. A protective layer 527 may be applied over the contact pad 523. At an operation 532, wet etching of the excess contact material is shown. At an operation 534, lithography and plasma etching for the release holes 531 is shown using a protective mask 529. At an operation 536, lithography and etching for the dicing lanes 533 using a protective mask 535 are shown. At an operation 538, which may be optional, lithographic covering 537 of the dicing lanes 533 is shown. At an operation 540, which may be optional, xenon difluoride etching of the sacrificial layer 513 is shown. At operation 542, which may be optional, a thin oxide layer 541 is applied over all exposed surfaces using an Atomic Layer Deposition (ALD) process. At operation 544, either a physical vapor deposition process of polytetrafluorethylene (PTFE) 543 or an ALD of perfluorodecyltrichlorosilane (FDTS) is applied over all exposed surfaces. The transducer elements may be diced along the dicing lanes 533.

Operating Parameters

The ultrasound transducers described herein generally have operating parameters such that they may send and receive ultrasound energy through a gaseous medium, such as air, to the material or surface to be characterized. Accordingly, the ultrasound energy delivered to the material or surface to be characterized may be sufficiently intense, may comprise a plane wave with spatial extent to match the material to be characterized, and/or may comprise sufficient phase stability across the spatial extent of the planar wave for measurements of the reflected phase to be measured. Another consideration may be size. Each of intensity, spatial coherence, divergence, and phase may be affected by making a device smaller.

An ultrasound transducer may be connected electrically connected to a digital processing device as described herein. The digital processing device may control various aspects of the transducer elements and ultrasound transducers as disclosed herein. For example, a system may comprise a digital processing device, an analog to digital converter, an analog "front end", and the transducer. Sometimes the system may further comprise a mechanical layer between the transducer and the object to be ultrasonically interrogated, which constitutes for example a quarter wavelength matching layer. The digital processing device may provide a driving waveform for the ultrasound transducer. For example, the digital processing device may provide a driving waveform for the excitation device. For example, the digital processing device may receive a waveform from the transducer corresponding to the reflected ultrasound signal from the device.

Communication between the transducer and digital processing device may be mediated by a digital-to-analog converter (DAC). An ultrasound transducer may have an average capacity and resistance voltage, sufficient to couple to the DAC. For example, the capacity of the ultrasound transducer may be between 2.5 picoFarad (pF) and 10.0 pF. For example, the capacity of the ultrasound transducer may be less than 50 pF, less than 20 pF, less than 10 pF, less than 5 pF, less than 2 pF, less than 1 pF, or any capacitance within a range given by any two of the preceding values.

For example, the resistance of the ultrasound transducer between 0 and 10 kHz frequency may be between 1 and 150 megaOhms (MΩ). For example, the resistance of the ultrasound transducer may be less than less than 10 MΩ, less than 5 MΩ, less than 2 MΩ, less than 1 MΩ, less than 0.5 MΩ, less than 0.2 MΩ, less than 0.1 MΩ, less than 0.05 MΩ, less than 0.02 MΩ, less than 0.01 MΩ or any resistance within a range given by any two of the preceding values.

A driving waveform may be electrically transmitted from the DAC to the ultrasound transducer via the contact pads of the transducer. In cases where the transducer elements are commonly connected to the same pad, the driving waveform may be transmitted via the pad to each top or bottom electrode of each element. Each transducer element may respond to the driving waveform based on the physical characteristics of the element itself and the fidelity of the waveform transmitted to the transducer. Each element may transmit ultrasound signal in response to the driving waveform. The transducer may transmit ultrasound signal corresponding to a sum of transmitted ultrasound signals of the elements.

Application of a voltage to each ultrasound transducer element may cause the working surface of the transducer element to deflect. In some cases, a bias voltage is maintained. In some cases, the bias voltage may not exceed a pull-in voltage. With sufficient voltage the working surface may deflect to the bottom surface of the transducer cavity, which may damage the transducer. The ultrasound waveform may be generated by a second signal which is an oscillating voltage at the carrier frequency and may augment the bias voltage. If the duty cycle is low, then the oscillating voltage with the bias voltage together may in some cases exceed the maximum pull-in without consequence. In some cases, a large oscillation voltage which is unipolar may be used. The unipolar oscillation voltage with the bias may result in a lower net voltage.

The voltage may be within a working range deliverable by driving circuitry of the ultrasound transducer. For example, the ultrasound transducer may have an 80% pull-in voltage of less than about 60V, 50V or less. For example, the ultrasound transducer may have an 80% pull-in voltage of less than about 45V.

The degree of deflection for each element per unit voltage may be controlled by the material of the plate layer, by the thickness of the plate layer, by the radius of the plate layer, by the holes in the plate layer, by the gap height below the plate layer, etc. The response time between application of a voltage and deflection may be affected by the distance between the transducer and the DAC, by the frequency bandwidth of the transducer, etc.

Operating frequencies of a cMUT may be varied with the driving circuitry; however, operable ranges of operating frequencies may be determined by the geometries and composition of the transducer elements themselves. For example, the operating frequency may be affected by the size of the working surface of the transducer element, by the release hole geometry, by materials used to form the individual elements, etc. Each transducer element may comprise a resonant frequency at which the transducer is more responsive. Each transducer element may also be responsive at a range of frequencies. The range of frequencies at which the ultrasound transducer is operable may be referred to as the bandwidth.

The bandwidth of the ultrasound transducer may relate to the response time of the transducer to an application of a driving voltage. For example, if the applied voltage is a square wave excitation. A transducer with a larger bandwidth may better reproduce the higher frequency components of the square wave leading to a squarer transmitted waveform. The bandwidth of the ultrasound transducer may be an important factor in building an air coupled cMUTs. In an example, if the spreading of the frequency components is too large, beating oscillations may result in the tails of the receive signal. In an example, the ultrasound transducer has a frequency bandwidth of plus or minus 5% of center frequency at full width at half maximum. In some cases, the bandwidth of the transducer may be characterized by a frequency sweep measurement. In an example, the fractional bandwidth of the ultrasound transducer may be greater than 10%. The fractional bandwidth of the ultrasound transducer may be related to the range of frequencies which may be produced by the transducer. Higher bandwidth transducers may be tunable over a larger frequency band. The phase characteristics may place a functional upper and lower limit on transducer frequency for a particular transducer configuration. In some cases, high ultrasound frequency may correlate with lower beam spread. Transducers of the present disclosure may have a center frequency between 1 MHz and 3 MHz. Transducers of the present disclosure may have a center frequency greater than 1 MHz. Transducers of the present disclosure may have a center frequency greater than 2 MHz.

A functional transducer may have sufficient reflected intensity at the transducer to measure the oscillation of the tympanic membrane while being below a threshold to damage the tympanic membrane. In other cases, a functional transducer may have sufficient reflected intensity at the transducer to measure the oscillation of the surface to be characterized while being below a threshold to damage that surface. Certain media or reflecting surfaces themselves may be particularly more absorptive. For example, when there is significant impedance mismatch between the reflecting surface the propagation medium, there may be significant ultrasound absorption (e.g., tissue and air). The intensity of the ultrasound beam may be attenuated, for example, due to diffraction loss. Diffraction losses may be reduced with better phase coherence in the transmitted ultrasound beam.

Additionally, the intensity of the ultrasound beam may be tailored to the application. For example, the intensity of the ultrasound must be sufficiently small so as not to present a safety hazard to the eardrum or the hearing mechanism. For example, the ultrasound intensity must be sufficiently large that a reflected ultrasound signal may be measured. In an example, the ultrasound transducer has a projected peak acoustic pressure of about 40 Pa or less or 20 Pa or less measured at a distance of 15 mm to from the transducer, along the axis of the main lobe of the ultrasound beam. The ultrasound transducer can have a peak acoustic pressure of about 40 Pa to 250 Pa measured at a distance of 25 mm from the transducer, along the axis of the main lobe of the ultrasound beam. The ultrasound transducer can have a peak acoustic pressure of about 20 Pa to 120 Pa measured at a distance of 12.5 mm from the transducer, along the axis of the main lobe of the ultrasound beam.

It may be advantageous for an ultrasound transducer to be operable in an absorptive medium. For example, transducers of the present disclosure may be operable when diffraction losses may be between 20 and 40 dB (round trip) for a target at distance 12.5 mm to 25 mm from the transducer, along the axis of the main lobe of the ultrasound beam. In an example, the ultrasound transducer has an attenuation loss (round trip) through the gaseous medium of more than 45 dB measured at a distance 12.5 mm to 25 mm from the transducer, along the axis of the main lobe of the ultrasound beam.

It may be advantageous for an ultrasound beam to be sufficiently divergent to illuminate a target. It may also be advantageous for an ultrasound transducer to be sufficiently narrow (directional) to avoid attenuation loss. In an example, the ultrasound transducer may produce an angular beam spread through a gaseous medium of less than 15 degrees. In an example, the ultrasound transducer may produce an angular beam spread between 10 and 20 degrees, within a 1.2 to 1.8 MHz bandwidth and for a transducer edge length between 0.6 and 1.0 mm. The angular beam spread may be affected by the phase characteristics of the ultrasound transducer elements relative to one another. For example, diffractive losses may occur when one or more transducer elements are out of phase or partially out of phase relative to the average of all elements of the transducer.

It may be advantageous for an ultrasound transducer to have sufficient signal to noise to detect the phase of the reflected waveform from target tissue. The signal to noise ratio may decrease with increasing distance traveled by the ultrasound waveform. For example, the detected signal may decrease due to losses through the gas transmission medium. Such decreases may be diffractive, may be absorptive, etc. For example, if the ultrasound beam is divergent, the reflected ultrasound detected may similarly be decreased. The devices disclosed herein may exhibit a signal to noise ratio greater than 30 dB (round trip) measured at a target distance of 12.5 mm to 25 mm along a primary transmission axis of the transducer.

Surface Characterization

The transducer described herein may be used to characterize surfaces and materials adjacent the surfaces. The transducer can be configured to be operated in many modes, for example, any one of the following ultrasound modes: A-mode, B-mode, M-mode, or Doppler mode. A mode is the simplest type of ultrasound. A transducer scans a line through a target with echoes plotted on a screen as a function of depth. B mode requires a linear array of transducers that simultaneously scan a plane through a target that can be viewed as a two-dimensional image. In some embodiments, a plurality of the transducer devices may be provided and arranged in a linear array for B mode opera ration. M-mode requires a rapid sequence of A- or B-mode scans which are organized in a plot to allow a user to view and measure a range of motion of a target. Doppler mode makes use of the Doppler effect in measuring a visualizing fluid flow. By calculating a frequency shift of a target volume, the speed and direction can then be determined and visualized graphically using spectral Doppler, as an image using directional Doppler or non-directional power Doppler. In some embodiments, one or more of the transducer devices described herein may be placed adjacent a moving object or fluid, for example, a blood vessel with circulating blood therein, in a Doppler mode to determine movement-related characteristics and/or properties.

Referring to surface characterization in particular, a low frequency excitation source may generate a movement of the surface or membrane during an interval. This interval may be coincident with acoustic wave delivered by an ultrasound transmitter to the surface or membrane. This excitation may be continuous, may be pulsed, etc. The ultrasound reflected from the surface may be received at a transducer. This transducer may be the same transducer that generated the incident acoustic wave. The displacement of the surface or membrane may be related to a phase change in the received signal when compared to the transmit signal. The movement of the membrane may affect a phase change. This displacement may vary with time. An analysis of the temporal displacement of the surface or membrane, as measured by the phase shifts of the reflected ultrasound in response to the pneumatic excitation coupled to the surface or membrane may be used to determine the mechanical characteristics of the surface or membrane, or the underlying material on the far side of the surface. This information may be used in combination the temporal displacement measured from templates of other membrane response to create a comparison. This information may be used in combination with other metrics associated with the delay in and amplitude of response of the surface or membrane to the low frequency excitation source. The mechanical characteristics measured may include a non-contact measurement of the mechanical properties the fluid below the surface or membrane may be determined.

In some embodiments, an elasticity of a surface may be measured. The phase and/or amplitude of the reflected ultrasound may be analyzed to produce elasticity metric. The elasticity measurement may characterize a series of measurements in response to an applied excitation. The elasticity metric may be derived from the response of the surface and may provide an indication of one or more of several different phenomena. For example, the elasticity metric may indicate whether a surface adjacent to a membrane has a gaseous boundary (in which case the reflection is from the membrane itself) or fluid boundary (in which case the reflection is from both the membrane and fluid adjacent to the membrane). In an example, the elasticity metric may indicate, for the case of characterizing a fluid behind the membrane fluid boundary, the extent or a characteristic of the fluid. In some examples, the elasticity metric may be used to measure the characteristics of an elastic fluid with or without hysteresis of response. In a fluid with a hysteresis response, the fluid may exhibit an offset in displacement response, or "memory," such that the response behavior in one direction is similar to the response behavior in the opposite direction, but only after traveling a particular displacement distance. For a hysteresis response, it may be necessary to characterize the linear behavior of the response after a particular measured displacement associated with the hysteresis of the system. A fluid elasticity metric may be determined from the characteristic response of the surface or membrane to the surface excitation and reflected ultrasound characterization. There also may be an asymmetry in the response of the surface to the low frequency stimulus. If the fluid underlying a membrane exceeds a normal volume, then the membrane may be in a distended state and less disposed to motion in a direction towards the transducer compared to a motion away from the transducer. Contrarily, if the fluid underlying the membrane is below a normal volume, then the membrane may be in a retracted state and less disposed to motion in a direction away from the transducer compared to a motion towards the transducer.

In some embodiments, a surface deflection may be estimated. For example, the estimate of surface deflection may be derived from a measured estimate of velocity, acceleration, or any other metric associated with deflection over time. For example, a displacement of the surface will result in a shortened path from the transducer to the surface, and the reflected signal from the surface back to the transducer will return with a phase shift. The phase shift of the reflected ultrasound relative to an excitation thus confers information about an amount of deflection. With an estimate of the force applied by the excitation, an estimate of the elasticity of the membrane can be estimated.

In one example, the excitation is a step or impulse response with a rising edge, falling edge, or impulsive excitation. The impulse excitation starts an oscillating deflection of the membrane. The reflected ultrasound can be measured from the time of excitation through the damping period of the oscillation of the membrane. In some embodiments, an estimate of elasticity or viscosity may be performed by examination of a ringdown characteristic. For example, the ringdown characteristic may comprise at least one of an exponential decay time or a ring cycle interval or frequency, such as the decomposition of a response into a ringdown characteristic, such as:

$$\phi(t) = e^{-t/\tau} \cos(2\pi f t)$$

where:
$\phi(t)$ is the captured phase for a series of measurements;
$\tau$ is the exponential decay coefficient;
f is the ring cycle frequency; and
t is time.

The damping constant of the oscillator may relate to energy lost from the membrane into the surrounding environment. In an example, if the membrane is adjacent to a fluid, the fluid may damp the oscillation of the membrane. The viscosity of the fluid may relate to the damping of the oscillator. The ring cycle frequency may relate to the restoring constant of the elastic membrane. The restoring constant may be related to the elasticity of the membrane. The restoring constant may be related to the viscosity of a fluid adjacent the membrane. The ring cycle frequency may be higher the lower the viscosity of a fluid adjacent the membrane.

Each excitation event may start a new deflection of the membrane. For example, an impulse excitation may pull the membrane in or push the membrane out for a limited period of time. For example, a square wave excitation may pull the membrane in or push the membrane out for a longer time. For example, a sine wave or other more complex excitation may be applied and the observed ringdown at the transducer may be a cross-correlation of the excitation field with the responding field.

Applications

The transducers, transducer elements, and methods of use and manufacture thereof may be used to characterize a number of biological tissues to provide a variety of findings which inform a medical diagnosis. A biological tissue may comprise a patient organ. A speculum may be disposed within a bodily cavity to position one or more transducers to characterize a patient tissue. Once in position, the transducer may be operated in any of the modes described herein to characterize the patient tissue. A patient organ or bodily cavity may comprise for example: an ear canal, muscles, tendons, a mouth, a tongue, a pharynx, an esophagus, a stomach, an intestine, an anus, a liver, a gallbladder, a pancreas, a nose, a larynx, a trachea, lungs, a kidneys, a bladder, a urethra, a uterus, a vagina, an ovary, testes, a prostate, a heart, an artery, a vein, a spleen, a gland, a brain, a spinal cord, a nerve, etc.

In an example, the transducers, transducer elements, and methods of use and manufacture thereof may be used to characterize an animal or human organ such as the ear. For example, the transducer may be provided on a speculum and positioned within the ear canal. An excitation generator may apply an impulsive pressure to the tympanic membrane, the transducer may direct ultrasound to the tympanic membrane, and reflected ultrasound energy may be measured from the surface of tympanic membrane. The phase changes of the reflected ultrasound during application of the non-contact excitation and/or after removal of the non-contact excitation may indicate an elasticity which may be correlated to the type of fluid behind the tympanic membrane, e.g., air, indicating a healthy ear, clear fluid, indicating a viral infection, or opaque fluid, indicating a bacterial infection, as further described herein.

In another example, the transducers, transducer elements, and methods of use and manufacture thereof may be used to characterize an animal or human organ such as the eye. For example, the excitation generator may apply an impulsive pressure to an eye, the transducer may direct ultrasound to the eye, and reflected ultrasound energy may be measured from the surface of the eye. The phase changes of the reflected ultrasound during application of the non-contact excitation and/or after removal of the non-contact excitation may indicate an elasticity which may be correlated to an inter-ocular pressure for measurement or diagnosis of glaucoma.

In another example, the transducers, transducer elements, and methods of use and manufacture thereof may be used to characterize an animal or human lung. For example, audio tones from the chest (for example, at a frequency of 3-20 Hz) could be demodulated from the transducer. The transducer could be integrated into a stethoscope-like device wherein the transducer can be moved up the chest during a "knock test" (auscultation) to identify a change in the reflected ultrasound which can indicate fluid in the lungs (e.g., mucus or water). In some embodiments, a plurality or array of transducers may be provided and placed or worn on the chest. The phase changes of the reflected ultrasound during application may indicate a change in fluid viscosity which may be correlated to a lung disease such as pneumonia, lung cancer, chronic obstructive pulmonary disease (COPD), idiopathic pulmonary fibrosis (IPF), etc.

The transducers, transducer elements, and methods of use and manufacture thereof may be used for example, to characterize a food item. For example, the excitation generator may apply an impulsive pressure to the surface of a food item such as a vegetable or fruit, and the ultrasound energy may be applied to the food item to measure the time dependent surface response of the fruit or vegetable, to determine an elasticity or other physical property which may be correlated to the ripeness of the fruit or vegetable. For example, the food item may be placed into a holder and the surface excited with a puff of gas such as air, the surface deflection response estimating ripeness or other property. For example, the excitation may be a gas which may be delivered at a supersonic velocity and/or at a glancing angle to the surface of the food item, or one or more food items may be placed into a chamber which has a variable pressure to measure a low frequency surface response to pressure, such as deflection vs. pressure. For example, the excitation may be applied to one surface and the response measured on a different surface of the same item, such as the measurement of a propagating surface wave or a shear wave which travels through the item being characterized.

The transducers, transducer elements, and methods of use and manufacture thereof may be used to characterize an industrial process. For example, the small size of the transducer disclosed herein can be applied to any industrial process wherein larger transducers, ultrasound, or other modalities such as LIDAR are prohibitive due to their large size. The high resolution achieved by the presently disclosed transducer at short ranges, e.g. less than 25-35 millimeter range, with 10-20 micrometer movement (e.g., via Doppler integration) allows the present invention to be applied to a wide array of industrial processes wherein analysis without physically touching the analyte is necessary. For example, the excitation generator may apply an impulsive pressure to the surface of a manufactured part such as to determine the consistency of a viscous fluid such as a lubricant, and the ultrasound energy may be applied to the part to measure the time dependent surface response of the viscous fluid, to determine an elasticity or other physical property which may be correlated to quality of the lubricant. The transducer may be used to measure the thickness of paint by comparing a painted section of an object to an unpainted section. The transducer may be used to measure whether a painted object is dry by comparing a painted object to a similar object that has been recently painted with an identical paint. The transducer may be used as a part of a manufacturing process to identify an object as a part of counting the objects being manufactured. The transducer may be used to measure a change in density or composition of an object by comparing an object that has undergone a process to an object before the process (e.g., cooked food items, curing processes, etc.). Other industrial examples may include range finding applications, ultrasonic transit-time gas flow meters for metering dynamic gas flows, anemometry applications, and various other ultrasound-based sensing applications.

Otoscope Device

The transducers, transducer elements, and methods of use and manufacture thereof may be used to characterize a tympanic membrane. For example, a membrane may be characterized to determine a condition of an ear, such as acute otitis media (AOM). A characterization that an ear exhibits AOM may include detection of the presence of effusion and characterization of the type of effusion as one of serous, mucoid, purulent or combinations of these. In AOM, the middle ear effusion (MEE) may be induced by infective agents and may be thin or serous with viral infection and thicker and purulent with bacterial infection. Accordingly, determining the viscosity of a fluid adjacent a tympanic membrane may provide information which may be used to characterize a membrane.

Figure 6A:
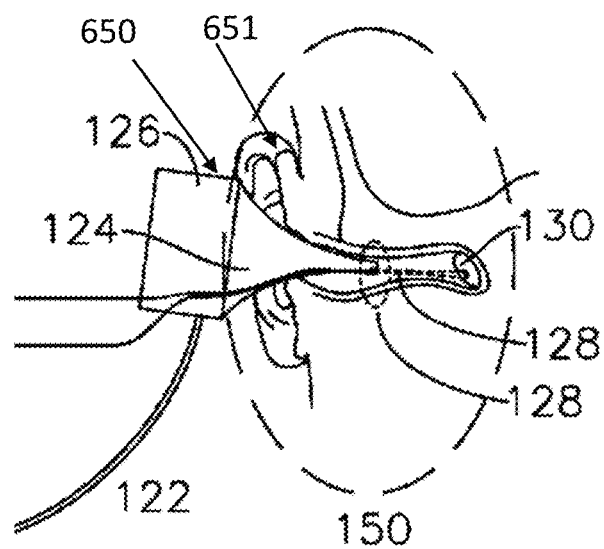
FIG. 6A illustrates a side section view of a speculum of an otoscope disposed within an ear, in accordance with some embodiments.
Figure 6B:
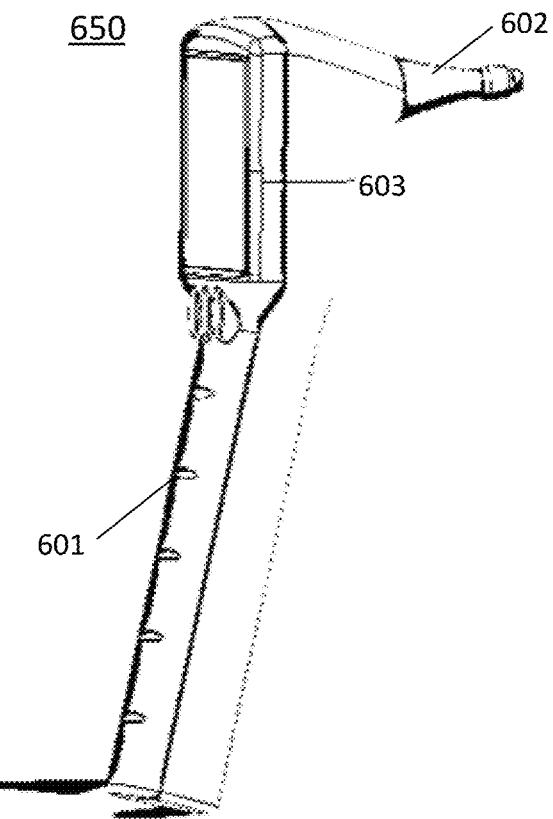
FIG. 6B illustrates a front section view an otoscope of the present disclosure, in accordance with some embodiments.

FIG. 6A illustrates a side section view a speculum of an otoscope 650 disposed within an ear 651, in accordance with some embodiments. FIG. 6B illustrates a front section view of an otoscope 650 of the present disclosure, in accordance with some embodiments. Region 150 (shown in magnified view FIG. 6A) illustrates a cross section view of a middle ear and tympanic membrane 130 of a subject being examined. The tympanic membrane 130 may be interrogated by an ultrasound beam 128 from an ultrasound transducer. The transducer may be mounted on the inner surface of a speculum tip 124. The speculum tip may be detachable from an otoscope 650 via speculum mounting adapter 126. The speculum tip may be operably coupled or include an excitation generator. In some cases, the excitation generator may create a pressure excitation. In some cases, the excitation generator may create pressure excitation which is a sonic excitation, a sub-sonic excitation, or a super-sonic excitation. The pressure excitation generated by the excitation generator may be an impulsive step or delta (impulse) generation, a sinusoidal pressure excitation, a square wave excitation, or any combination of these, and the excitation may be a gated burst or continuous. The pressure excitation may be provided with or without a static positive or negative pressure bias.

In some examples, the excitation generator creates a pressure excitation, such as an air puff. For instance, the otoscope mounting adapter 126 and speculum tip 124 may have a common interior volume. The common interior volume may provide for coupling of dynamic pressures from an excitation generator through a coupling 122 to the ear canal where the air pressures result in displacement of the tympanic membrane 130. The excitation generator may generate pressure variations which are coupled into the ear canal through the speculum tip 126.

In some examples, the excitation generator may be an air bladder manipulated by an operator to apply a force to a membrane or surface, an air displacement generator producing alternating pressure, step pressure, or air puffs. The excitation generator output may be sealed to the surrounding region of the surface or unsealed and using a puff of gas such as atmospheric air or other suitable gas.

In some examples, the excitation generator may produce a sonic excitation, a sub-sonic excitation, or a super-sonic excitation. For example, the excitation generator may produce a sub-audio frequency below 20 Hz, an audio frequency from 20 Hz to 20 KHz, or a super-audio frequency above 20 KHz. In an example, a sonic excitation, a sub-sonic excitation, or a super-sonic excitation may be produced by a piezoelectric transducer. The piezoelectric transducer may convert an electrical signal to a physical displacement which may in turn induce a pressure wave. In an example, a sonic excitation, a sub-sonic excitation, or a super-sonic excitation may be produced by a cMUT transducer. In an example, an audio speaker with a voice-coil actuator may be used to produce an excitation.

An ultrasound transducer may be provided within the otoscope in addition to and distinct from the excitation generator. The ultrasound transducer may comprise a variation, example, or embodiment of any transducer element or ultrasound transducer disclosed herein. In some cases, the ultrasound transducer and the excitation generator may be the same element.

As shown in FIG. 6B, the otoscope may comprise a handle 601 for positioning of the speculum 602. The otoscope may include a video display 603. The display may display to a user an optical image of the membrane to be characterized. The display 603 may show an ultrasound image. The display 603 may provide a user interface in which to control various aspects of the otoscope 650 and/or analysis of the ultrasound data. The otoscope may comprise a digital processing device on board, for example, within a handle 601 of the device. The otoscope may connect to a remote device such as a server, a remote memory, a remote processing device, etc. The analysis of the ultrasound data may be performed on board or remotely.

Figure 7A:
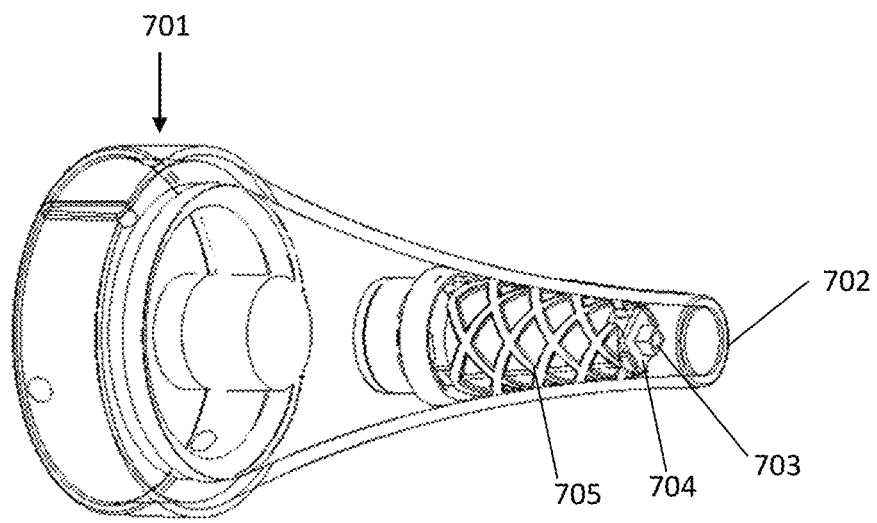
FIG. 7A illustrates a side section view of a speculum, in accordance with some embodiments.
Figure 7B:
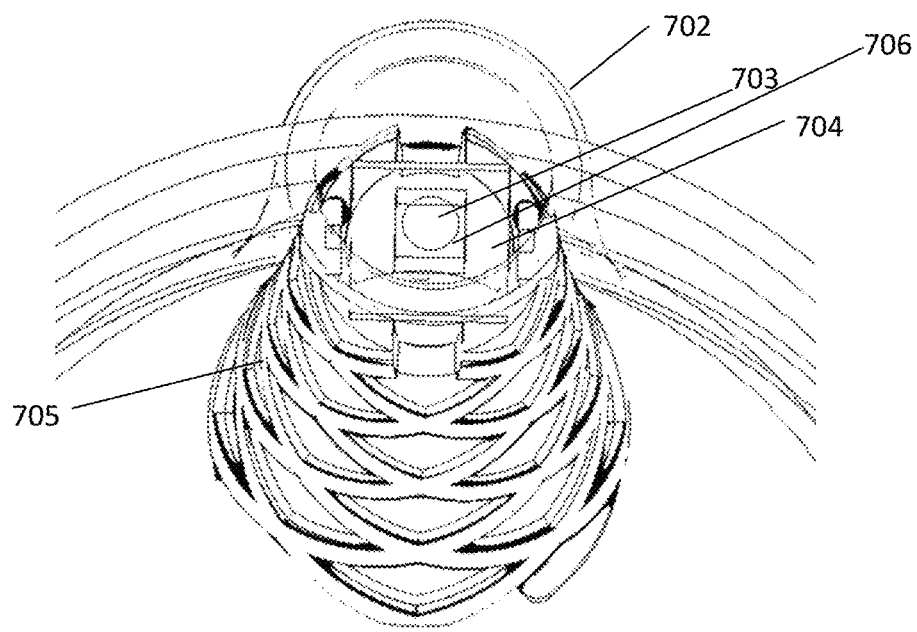
FIG. 7B illustrates a front section view of a tip of a speculum, in accordance with some embodiments.
Figure 10A:
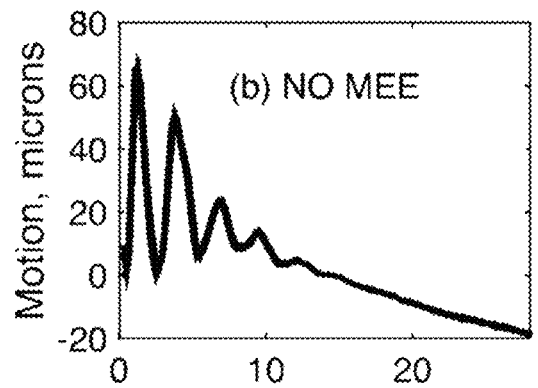
FIG. 10A, FIG. 10B, FIG. 10C, and FIG. 10D show example plots of mobility measurements for a membrane in the presence of fluids of four different viscosities, in accordance with some embodiments.
Figure 10B:
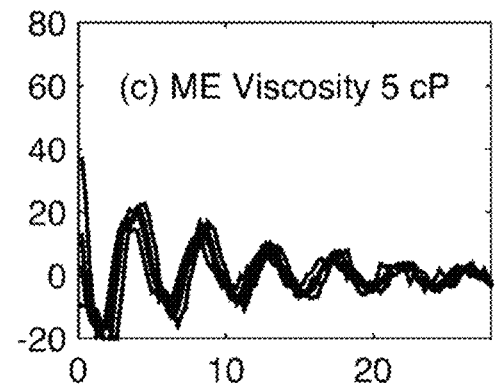
Figure 10C:
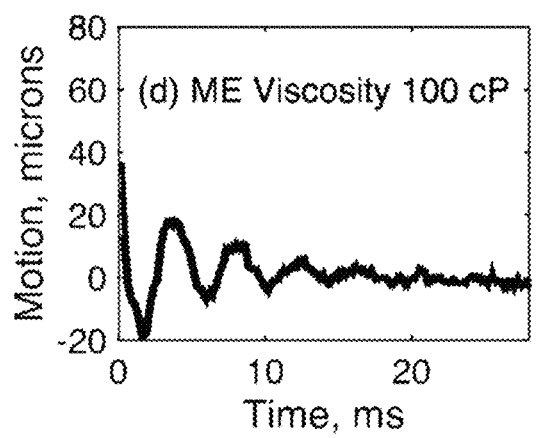
Figure 10D:
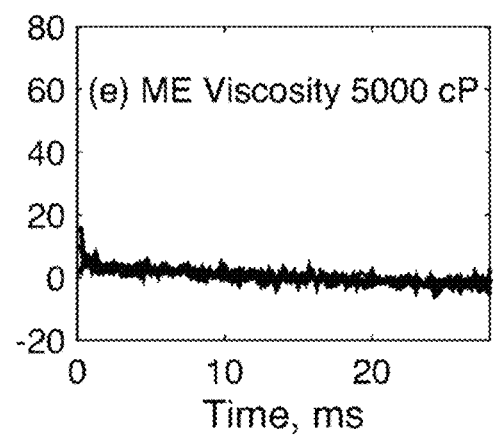

FIG. 7A illustrates a side section view of a speculum 701, in accordance with some embodiments. FIG. 7B illustrates a front section view of a tip of a speculum 702, in accordance with some embodiments. In some examples, the ultrasound transducer 703 is disposed within the speculum 701. The speculum may be disposable. The speculum may comprise an ultrasound transducer 703 disposed near a tip region 702 of the speculum 701. The speculum may comprise a lens assembly 704 which may aid in providing optical images to a user to guide positioning of an ultrasound transducer. In some examples, the ultrasound transducer 703 may be at the center of the speculum, and the optical sensing is consequently accomplished around the ultrasound transducer 704. The ultrasound transducer may be supported by a mesh 705. The mesh 705 may allow transmission of electrical signals to a digital processing device.

Ultrasound transducers described herein may comprise a base 706. The base may be mounted within the speculum via a plate 704. The plate 704 may allow the transducer to be centered or approximately centered within the opening of the otoscope. The plate 704 may be optically transparent. In an example, the plate 704 is glass. The plate 704 may comprise one or more openings which may allow for a pressure excitation to be conveyed from the interior of the speculum tip to the exterior of the speculum tip. The plate 704 may comprise one or more electrically conductive portions to allow for a driving voltage and/or current to be supplied to the transducer. The plate 704 may comprise one or more insulating layers. The plate 704 may itself comprise conducting or insulating portions. The plate 704 may be insulating with conducting portions mounted thereon.

A method of using an ultrasound transducer of the present disclosure may include providing an ultrasound transducer; directing the tip of a speculum within a lumen adjacent the membrane; directing a perturbation to a surface of the membrane; measuring a reflected ultrasound signal from the surface of the membrane; and characterizing the viscosity or elasticity of the membrane in response to the perturbation and the reflected ultrasound.

EXAMPLES

Example 1—Otoscope Test Data

FIG. 8A and FIG. 8B show example data traces showing false color contour plots of membrane motion in response to a perturbation, in accordance with some embodiments. FIG. 8A shows distance from the transducer versus time on the axes, and the brightness of the display is the echo signal intensity. There is a bright echo at about 13 mm depth which is the tympanic membrane. The bright echo at 5 mm depth is a part of the external ear canal. FIG. 9A shows the pressure applied, in a time phased manner which corresponds to the observed ultrasound data in FIG. 8A, in the external ear canal as detected by a pressure sensor (black). The pressure axis is on the left and the units are not normalized in this case. FIG. 9A also contains the observed displacement of the tympanic membrane as the right hand axis describes the grey displacement profile, and the units (microns) are not normalized in this case. The position scale in FIG. 9A is greatly magnified over FIG. 8A, so a motion is observed that is 10s of microns based on the applied low frequency square wave pressure stimulus. Likewise, FIG. 8B and FIG. 9B similarly show the correlation of the tympanic membrane displacement in response to the same square wave pressure perturbation.

FIG. 10A, FIG. 10B, FIG. 10C, and FIG. 10D show example viscosity measurements for a membrane in the absence of a middle ear effusion (MEE) and for various viscosity effusions, in accordance with some embodiments. FIG. 10 shows a greatly magnified time axis on a bench top model of the ear drum. It is observed in the four panels there is a different oscillation response to a step change in pressure, based on the ringing content frequency and duration. The panels progress from air to thin fluid to thick fluid to "glue" ear. As shown, an increase in the damping term of the ring down correlates with increasing MEE viscosity. Also as shown, increasing frequency of the ring down correlates with decreasing MEE viscosity. In cases of acute otitis media (AOM), the MEE may be induced by infective agents. The MEE may be thin or serous with viral infection and thicker and purulent with bacterial infection. A characterization the type of effusion as one of serous, mucoid, purulent or combinations of these may be inferred based on the measured viscosity.

Example 2—cMUT Test Data

The following comparative examples relate to changes in various design elements of the ultrasound transducers and elements disclosed herein. The following are provided by way of example only and are not intended to be limiting. The following shows a first comparative example set of specifications for a cMUT element, Table 1. Additionally, output specifications for the first comparative example is also shown, Table 2.

TABLE 1

| Parameter | Symbol | Min | Typical | Max | Condition/Remark | Unit |
|---|---|---|---|---|---|---|
| Wafer | | | | | | |
| Diameter | | | 150.0 ± 0.3 or 200 ± 0.5 | | | mm |
| Growth method: cz crystal orientation: {100} ± 1° double-sided polished | | | | | | |
| thickness | | 650 | 675 | 700 | | μm |
| Layer definitions | | | | | | |
| Isolation layer 1 | | 900 | 1000 | 1200 | SiO$_2$ | nm |
| Bottom electrode | | 150 | 200 | 250 | TiAl | nm |

TABLE 1-continued

| Parameter | Symbol | Min | Typical | Max | Condition/Remark | Unit |
|---|---|---|---|---|---|---|
| Isolation layer 2 | | 150 | 200 | 250 | SiO$_2$ | nm |
| Sacrificial layer | | 700 | 800 | 1000 | a-Si | nm |
| Plate layer | | 400 | 500 | 600 | TiAl | nm |

TABLE 2

| Parameter | Symbol | Min | Typical | Max | Condition/Remark | Unit |
|---|---|---|---|---|---|---|
| Coupling media | | | Air | | | |
| Center frequency | | 1 | 1.8 | 3 | | MHz |
| Bandwidth | | 5 | 15 | 25 | −3 dB @ center frequency | % |
| Plate displacement (Max) | | 250 | 300 | 350 | | nm |
| Max Bias voltage | | 25 | 30 | 50 | | V |
| Max AC voltage | | 15 | 25 | 35 | | V |
| Component dimension | | | | | | |
| Width | | 0.75 | 0.9 | 1.2 | | mm |
| Height | | 0.8 | 1 | 1.3 | | mm |

The following shows a second comparative example set of specifications for a cMUT element.

TABLE 3

| Comparative Example 2 | | | | | |
|---|---|---|---|---|---|
| Wafer diameter | | 150 | | | mm |
| Wafer thickness | | 675 | | | μm |
| Isolation layer 1 | 990 | 1000 | 1100 | SiO$_2$ | nm |
| Bottom electrode | 180 | 200 | 220 | TiAl | nm |
| Isolation layer 2 | 280 | 300 | 320 | PE-Oxide | nm |
| Sacrificial layer | 800 | 850 | 900 | a-Si | nm |
| Plate layer | 490 | 520 | 550 | TiAl | nm |
| Pad contact area | 900 | 1000 | 1100 | Al | nm |

The following shows a third comparative example set of specifications for a cMUT element.

TABLE 4

| Comparative Example 3 | | | | | |
|---|---|---|---|---|---|
| Wafer diameter | | 150 | | | mm |
| Wafer thickness | | 675 | | | μm |
| Isolation layer 1 | 990 | 1000 | 1100 | SiO$_2$ | nm |
| Bottom electrode | 180 | 200 | 220 | TiAl | nm |
| Isolation layer 2 | 280 | 300 | 320 | PE-Oxide | nm |
| Sacrificial layer | 1080 | 1100 | 1120 | a-Si | nm |
| Plate layer | 490 | 520 | 550 | TiAl | nm |
| Pad contact area | 900 | 1000 | 1100 | Al | nm |

FIG. 11A and FIG. 11B show top views of example working surface designs for transducer, in accordance with some embodiments. For each of comparative examples 2 and 3, the each of the working surface designs in FIG. 11A were implemented and tested on separate wafers. Comparative example 2 was implemented and tested on a first wafer and a second wafer to duplicate the experiment. No significant variation was found between the first and second wafer.

The columns in FIG. 11A indicate transducer working surface diameters which were fabricated and tested (50 microns, 60 microns, and 70 microns). The rows indicate the release hole configurations that were fabricated for each working surface diameter. Example release hole arrangements include: 6 holes equally spaced radially on a 42 micron ring centered on the working surface, 6 holes equally spaced radially on a 52 micron ring centered on the working surface, 6 holes equally spaced radially on a 62 micron ring centered on the working surface, 12 holes equally spaced radially on a 42 micron ring centered on the working surface, 12 holes equally spaced radially on a 52 micron ring centered on the working surface, 12 holes equally spaced radially on a 62 micron ring centered on the working surface, 12 holes equally spaced radially on a 16 micron ring centered on the working surface, 12 holes equally spaced radially on a 30 micron ring centered on the working surface, 12 holes equally spaced radially on a 34 micron ring centered on the working surface, 12 holes equally spaced radially on a 52 micron ring centered on the working surface, and 12 holes equally spaced radially on a 62 micron ring centered on the working surface.

The rows also include release slits. Example release slit arrangements include: a slit with a 0.8 micron width and a 4 micron length and a slit with a 0.8 micron width and an 8 micron length. In each of the illustrated examples, the slits may be located 4 microns radially inward from the edge of the work surface of the transducer.

Figures 12A, 12B:
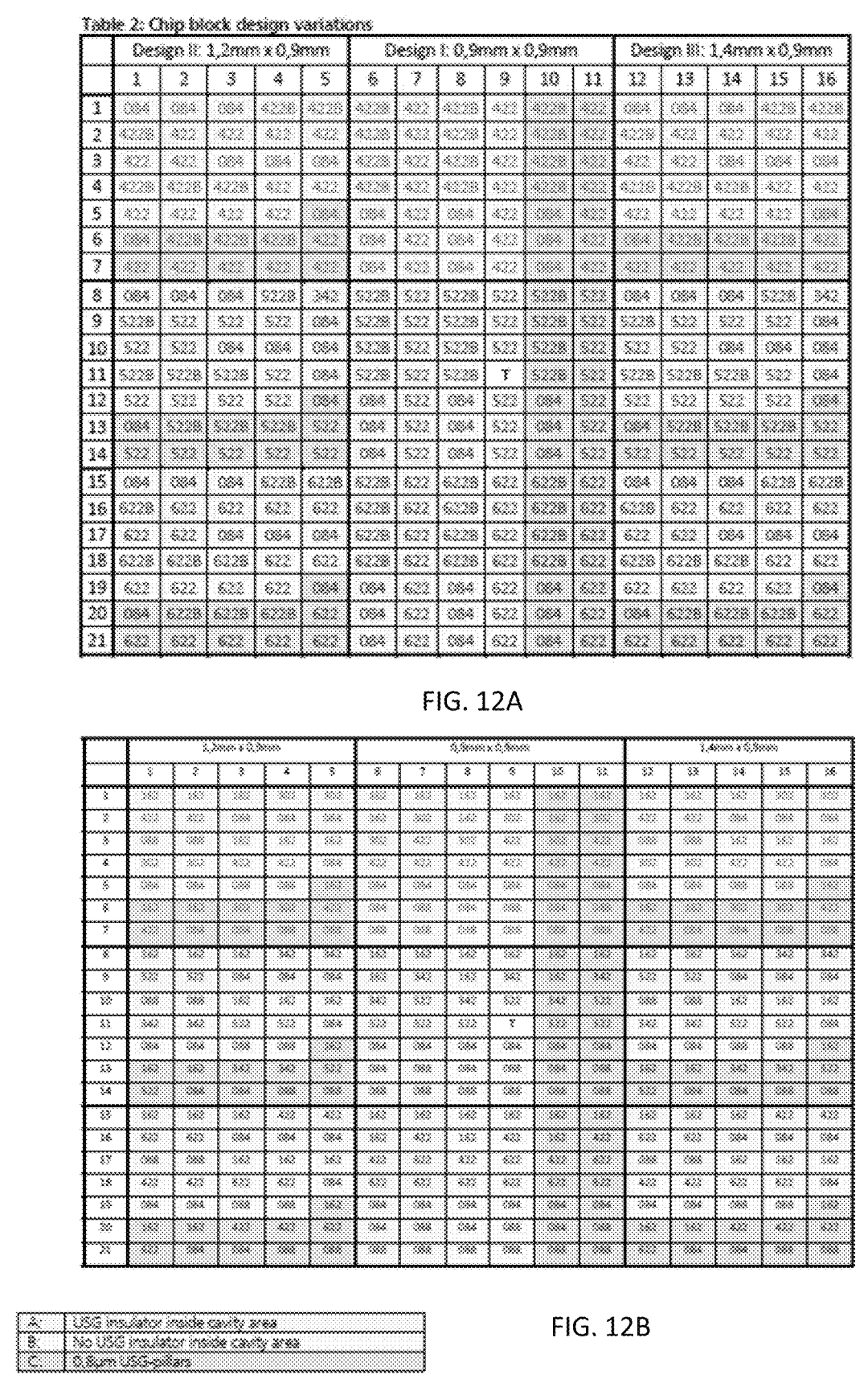

FIG. 12A and FIG. 12B show a table of the layout of tested example ultrasound transducer designs: Design I: 0.9 mm×0.9 mm, Design II: 1.2 mm×0.9 mm, Design III: 1.4×0.9 mm, in accordance with some embodiments. FIG. 12A and FIG. 12B indicate the working surface designs tested for each ultrasound transducer design. The shading indicates an interior characteristic of the cavity. The interior characteristics tested include: A: Insulator inside cavity, B: No insulator inside cavity, C: 0.8 micron pillars inside cavity. Each of FIG. 12A and FIG. 12B show a single layout that was repeated several times for a single wafer to account for variations across the surface of the wafer. On a single wafer 26 layouts may be repeated.

Figure 13A:
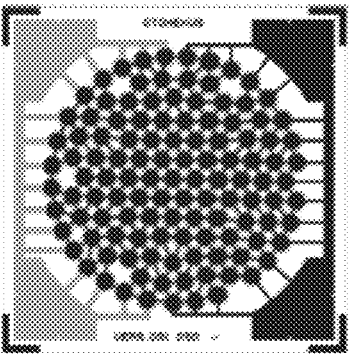
FIG. 13A, FIG. 13B, and FIG. 13C show schematics of ultrasound transducer configurations tested for each diameter transducer element tested, in accordance with some embodiments.
Figure 13B:
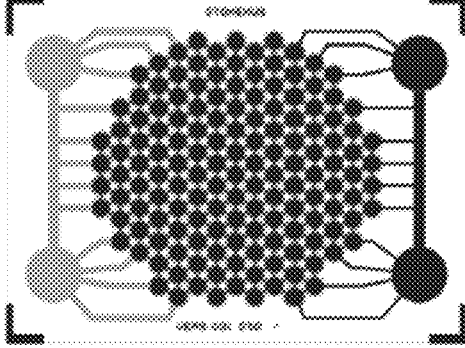
Figure 13C:
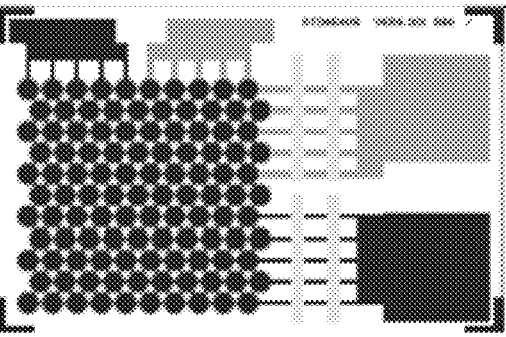

FIG. 13A, FIG. 13B, and FIG. 13C show schematics of the ultrasound transducer configurations tested for each diameter transducer element tested, in accordance with some embodiments. The ultrasound transducer designs include Design I: 0.9 mm×0.9 mm, Design II: 1.2 mm×0.9 mm, Design III: 1.4×0.9 mm. For each Design I, Design II, and Design III small variations are shown for each transducer working surface diameter. For each design, electrical contact pads and electrical connections are shown. Electrical connections and pads to the top electrode are shown in dark grey. Electrical connections and pads to the bottom electrode are shown in light grey.

FIG. 13A shows three variations of 0.9 mm×0.9 mm ultrasound transducers. In the first variation, 119 transducers with a 50 micron working surface diameter were arranged within a circular area with hexagonal closest packing structure. In the second variation, 85 transducers with a 60 micron working surface diameter were arranged within a circular area with hexagonal closest packing structure. In the third variation, 64 transducers with a 70 micron working surface diameter were arranged within a circular area with hexagonal closest packing structure.

FIG. 13B shows three variations of 1.2 mm×0.9 mm ultrasound transducers. In the first variation, 146 transducers with a 50 micron working surface diameter were arranged within a circular area with hexagonal closest packing structure. In the second variation, 102 transducers with a 60 micron working surface diameter were arranged within a circular area with hexagonal closest packing structure. In the third variation, 79 transducers with a 70 micron working surface diameter were arranged within a circular area with hexagonal closest packing structure.

FIG. 13B also shows a variation of a 1.4×0.9 mm ultrasound transducer. In the first variation, 156 transducers with a 50 micron working surface diameter were arranged within a rectangular area with hexagonal closest packing structure. FIG. 13C shows two more examples of a 1.4×0.9 mm ultrasound transducer. In the second variation, 110 transducers with a 60 micron working surface diameter were arranged within a rectangular area with hexagonal closest packing structure. In the third variation, 85 transducers with a 70 micron working surface diameter were arranged within a rectangular area with hexagonal closest packing structure.

For each transducer of each copy of each layout of each wafer a "pass" or "no pass" is assigned based on the following parameters measured at functional bias voltage. For example, a "pass" assignment may be based on the following table of measured frequency, capacity, and resistance.

TABLE 5

| Parameter | Symbol | Min | Typical | Max | Condition | Unit |
| --- | --- | --- | --- | --- | --- | --- |
| Resonant frequency | F | 1.6 | 1.8 | 2.0 | p = 1013 mbar<br>T = 27° C.<br>RH < 1% | MHz |
| Capacitance | C | 2.5 | | 10.0 | p = 1013 mbar<br>T = 27° C.<br>RH < 1%<br>100 kHz | pF |
| Resistance | R | 10 | | 150 | p = 1013 mbar<br>T = 27° C.<br>RH < 1%<br>100 kHz | MΩ |

FIG. 14A, FIG. 14B, FIG. 14C, FIG. 14D, FIG. 14E, and FIG. 14F show plots of frequency sweep measurements of the phase and impedance of ultrasound transducers tested herein, in accordance with some embodiments. A fractional bandwidth of the ultrasound transducer may be extracted from the measurements of FIG. 14A to FIG. 14F. Frequency sweep measurements are conducted at 80% of the pull-in Voltage for the relevant ultrasound transducer. The pull-in Voltage may vary for each type of ultrasound transducer tested. FIG. 14A shows a frequency sweep measurement of the phase of a 50 micron transducer element. FIG. 14B shows a frequency sweep measurement of the impedance of a 50 micron transducer element. FIG. 14C shows a frequency sweep measurement of the phase of a 60 micron transducer element. FIG. 14D shows a frequency sweep measurement of the impedance of a 60 micron transducer element. FIG. 14E shows a frequency sweep measurement of the phase of a 70 micron transducer element. FIG. 14F shows a frequency sweep measurement of the impedance of a 70 micron transducer element. As shown, each ultrasound transducer may have a characteristic resonance frequency. The bandwidth may also vary between each ultrasound transducer.

Figure 15A:
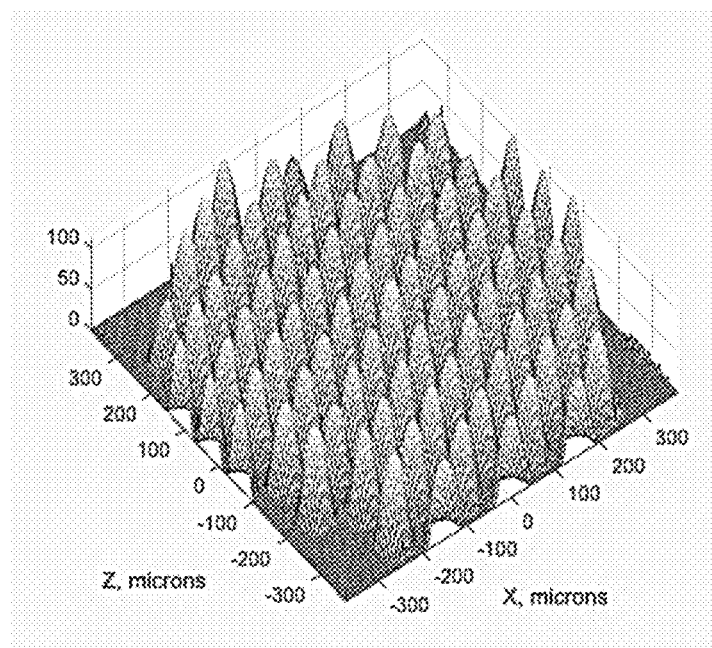
FIG. 15A and FIG. 15B show three-dimensional and two-dimensional plots, respectively, of normalized signal amplitude versus time and ultrasound transducer dimension using laser vibrometry, in accordance with some embodiments.
Figure 15B:
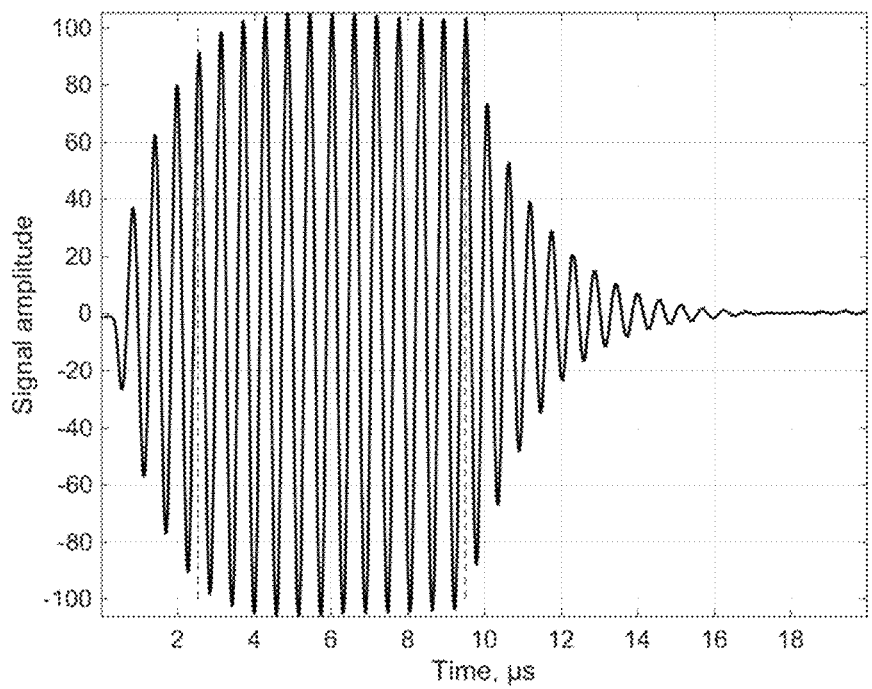

FIG. 15A and FIG. 15B show plots of normalized signal amplitude versus time and ultrasound transducer dimension using laser Doppler vibrometry (LDV), in accordance with some embodiments. As shown in FIG. 15A, LDV may be used to confirm the functionality of each element of an ultrasound transducer. These measurements may indicate that each transducer element represented by a peak in signal amplitude is vibrating. The LDV measurements may additionally be used to determine various operational parameters of the ultrasound transducer. Additionally, as shown in FIG. 15B, LDV may be used to characterize the frequency and phase each element in the ultrasound transducer relative to one another. FIG. 15B shows normalized signal amplitude versus time for a single transducer element. From these plots, the oscillatory frequency of each element at a particular driving voltage may be measured. The phase of the oscillations from each element may be compared to one another to analyze spatial coherence of the transmitted ultrasound.

Figure 16A:
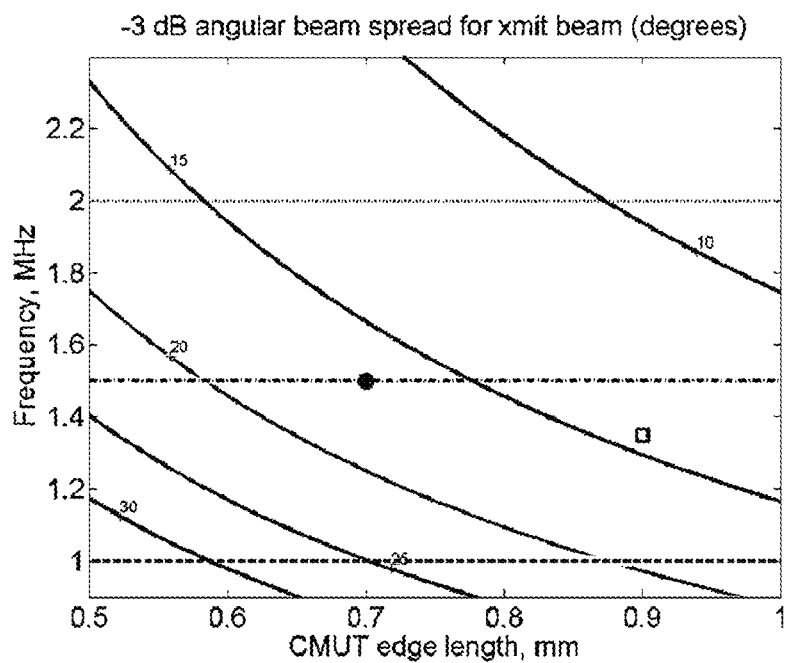
FIG. 16A and FIG. 16B show contour plots of the beam spread and ultrasound loss of a set of operable ultrasound transducers, in accordance with some embodiments.
Figure 16B:
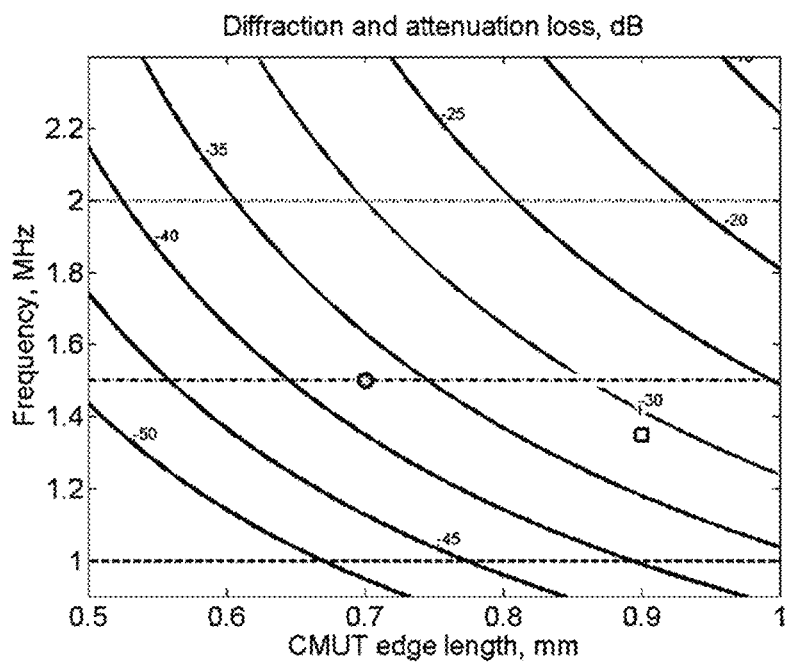

FIG. 16A and FIG. 16B show contour plots of the beam spread and ultrasound loss of a set of operable ultrasound transducers, in accordance with some embodiments. The devices shown have angular beam spreads between 10 and 20 degrees, within a 1.2 to 1.8 MHz bandwidth and for an edge length between 0.6 and 1.0 mm. Similarly, diffraction losses are between 20 and 40 dB measured at distance 12.5 mm to 25 mm normal to a working surface of the transducer elements.

FIG. 16A shows the relationship between ultrasound transducer edge length, central frequency, and beam spread. As shown, high frequency correlates with lower beam spread as does larger ultrasound transducer size. The size of the ear canal may place a functional upper bound on ultrasound transducer size. The phase characteristics shown in FIG. 14A, FIG. 14B, FIG. 14C, FIG. 14D, FIG. 14E, and FIG. 14F may place a functional upper (and lower) limit on transducer frequency for a particular transducer configuration. A functional transducer will have an ultrasound beam spot at the membrane to be characterized of roughly the size of the membrane or smaller.

FIG. 16B shows the relationship between ultrasound transducer edge length, central frequency, and beam attenuation/diffraction loss. As shown, high frequency correlates with lower loss as does larger ultrasound transducer size. The size of the ear canal may place a functional upper bound on ultrasound transducer size. The phase characteristics shown in FIG. 14A, FIG. 14B, FIG. 14C, FIG. 14D, FIG. 14E, and FIG. 14F may place a functional upper (and lower) limit on transducer frequency for a particular transducer configuration. A functional transducer will have sufficient reflected intensity at the transducer to measure the oscillation of the membrane while being below a threshold to damage an ear drum.

An optimal transducer may be subject to multiple constraints. The beam "spot" size needs to be not too big (e.g., such that SNR is lost) or too small (e.g., such that sensitivity to the target and difficulties aiming may be generated). Spot size may be affected by frequency (low frequencies may yield a bigger spot and higher frequencies a lower spot). Spot size may be affected by transducer edge length (high relates to a smaller spot, low to a bigger spot). The combination of these two parameters (frequency and edge length). The combination of these factors aa shown in FIG. 16A.

In combination with adjusting spot size, these factors may be related to the signal to noise ratio (SNR). Higher loss in FIG. 16B relates to lower SNR. As shown, improved transducers may operate s towards upper right of FIG. 16B and for example near the 15 deg contour in FIG. 16A.

Figure 17:
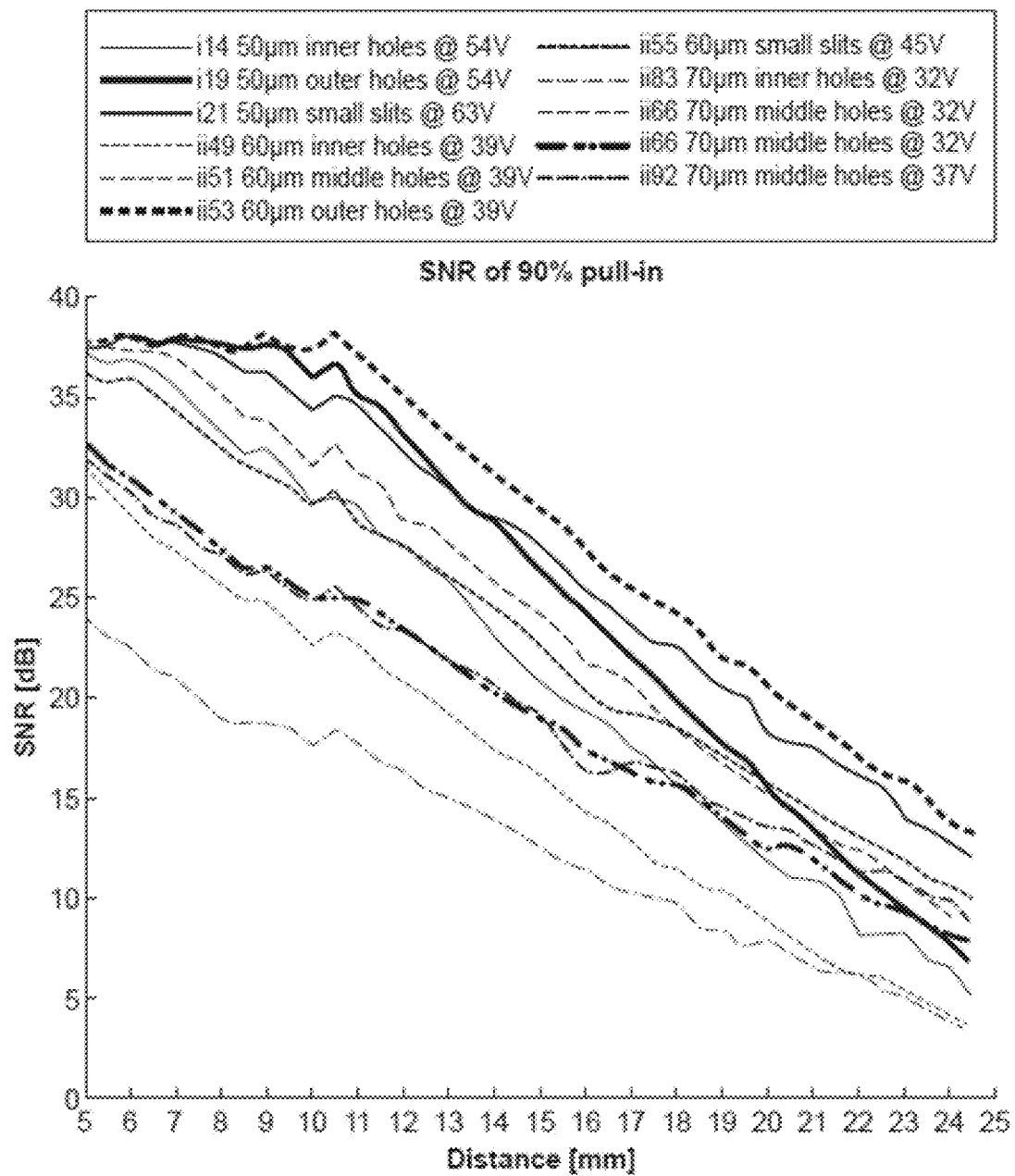
FIG. 17 shows a plot of the signal to noise ratio versus distance of a set operable ultrasound transducers, in accordance with some embodiments.

FIG. 17 shows a plot of the signal to noise ratio versus distance of a set operable ultrasound transducers, in accordance with some embodiments. As shown, the signal to noise ration decreases with increase distance traveled by the ultrasound waveform for all ultrasound transducer configurations. As shown, the 50 and 60 micron transducers with larger diameter release hole arrangements have relatively high signal to noise ratio. As shown, the devices may exhibit a signal to noise ratio greater than 15 dB at 80-90% pull in measured at a distance 12.5 mm to 25 mm normal to a working surface of the transducer elements.

Digital Processing Device

In some embodiments, imaging components, systems, and methods described herein include a digital processing device, or use of the same. For example, a digital processing device may be used to control various aspects of the transducer elements and ultrasound transducers described herein. For example, a digital processing device be used to store transmitted or received ultrasound waveform, to analyze received data, to apply current and/or voltage to a transducer, to convert analog signal from a transducer to a digital signal, etc. For example, a measurement device such as an otoscope device may comprise a digital processing device on board the device. The digital processing device may control various aspects of the otoscope, such as controlling the operation of the ultrasound transducer, analyzing data, transmitting data to a remote device, etc.

In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device may be optionally connected a computer network. In further embodiments, the digital processing device is optionally connected to the internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM).

In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 18:
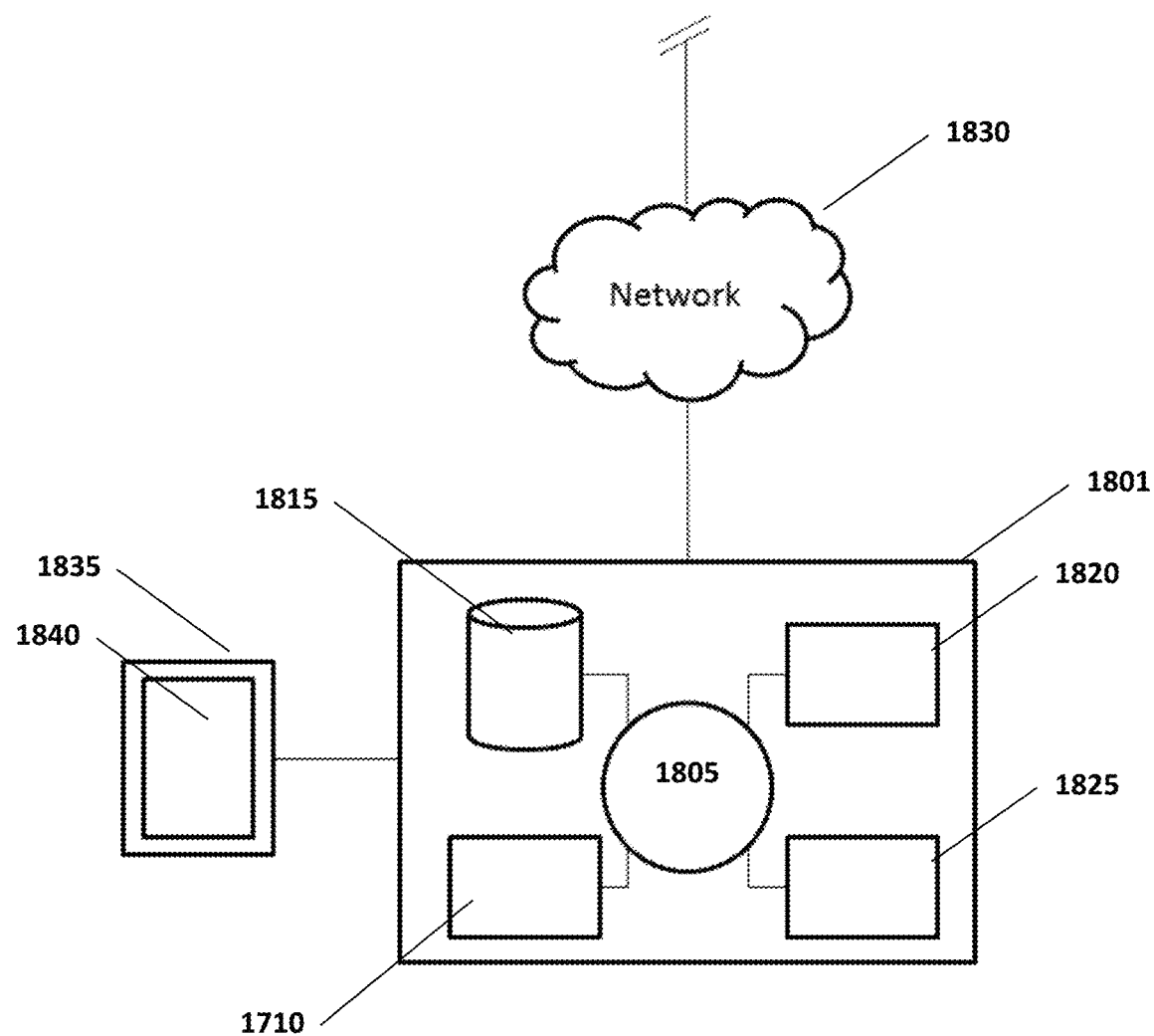
FIG. 18 shows a schematic of an ultrasound transducer system comprising a digital processing device and a display visible to a user, in accordance with some embodiments.

Referring to FIG. 18, in a particular embodiment, an example digital processing device 1801 is programmed or otherwise configured control to an imaging component and/or instruments as described herein. The device 1801 may regulate various aspects of the imaging component and/or instruments of the present disclosure, such as, for example, performing processing steps. In this embodiment, the digital processing device 1801 includes a central processing unit (CPU, also "processor" and "computer processor" herein) 1805, which may be a single core or multi core processor, or a plurality of processors for parallel processing. The digital processing device 1801 also includes memory or memory location 1810 (e.g., random-access memory, read-only memory, flash memory), electronic storage unit 1815 (e.g., hard disk), communication interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communication bus (solid lines), such as a motherboard. The storage unit 1815 may be a data storage unit (or data repository) for storing data. The digital processing device 1801 can be operatively coupled to a computer network ("network") 1830 with the aid of the communication interface 1820. The network 1830 can be the Internet, an internet and/or extranet, or an intranet and/or extranet that is in communication with the Internet. The network 1830 in some cases is a telecommunication and/or data network. The network 1830 can include one or more computer servers, which can enable distributed computing, such as cloud computing. The network 1830, in some cases with the aid of the device 1801, can implement a peer-to-peer network, which may enable devices coupled to the device 1801 to behave as a client or a server.

Continuing to refer to FIG. 18, the CPU 1805 can execute a sequence of machine-readable instructions, which can be embodied in a program or software. The instructions may be stored in a memory location, such as the memory 1810. The instructions can be directed to the CPU 1805, which can subsequently program or otherwise configure the CPU 1805 to implement methods of the present disclosure. Examples of operations performed by the CPU 1805 can include fetch, decode, execute, and write back. The CPU 1805 can be part of a circuit, such as an integrated circuit. One or more other components of the device 1801 can be included in the circuit. In some cases, the circuit is an application specific integrated circuit (ASIC) or a field programmable gate array (FPGA).

Continuing to refer to FIG. 18, the storage unit 1815 can store files, such as drivers, libraries and saved programs. The storage unit 1815 can store user data, e.g., user preferences and user programs. The digital processing device 1801 in some cases can include one or more additional data storage units that are external, such as located on a remote server that is in communication through an intranet or the Internet. The digital processing device 1801 can communicate with one or more remote computer systems through the network 1830. For instance, the device 1801 can communicate with a remote computer system of a user.

Examples of remote computer systems include personal computers (e.g., portable PC), slate or tablet PCs (e.g., Apple® iPad, Samsung® Galaxy Tab, etc.), telephones, Smart phones (e.g., Apple® iPhone, Android-enabled device, Blackberry®, etc.), or personal digital assistants.

Methods as described herein can be implemented by way of machine (e.g., computer processor) executable code stored on an electronic storage location of the digital processing device 1801, such as, for example, on the memory 1810 or electronic storage unit 1815. The machine executable or machine readable code can be provided in the form of software. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

The digital processing device 1801 can include or be in communication with an electronic display 1835 that comprises a user interface (UI) 1840. Examples of UI's include, without limitation, a graphical user interface (GUI) and web-based user interface. In some cases, electronic display 1835 may be connected to the computer system 1801 via a network, e.g., via network 1830.

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An ultrasound transducer comprising:
   a plurality of capacitive ultrasound transducer elements; and
   a base having a largest dimension sized and shaped to be disposed with an external ear canal, wherein the plurality of capacitive ultrasound transducer elements is mounted on the base;
   wherein the plurality of capacitive ultrasound transducer elements is configured to form an ultrasound waveform having an angular beam spread through a gaseous medium of greater than 15 degrees and an attenuation loss through the gaseous medium of greater than 10 dB measured at a distance from 12.5 mm to 25 mm along a primary transmission axis.

2. The ultrasound transducer of claim 1, wherein the largest dimension of the base is less than 3 mm.

3. The ultrasound transducer of claim 1, wherein the plurality of capacitive ultrasound transducer elements has a resonant frequency between 1.0 MHz and 3.0 MHz.

4. The ultrasound transducer of claim 1, wherein each of the plurality of capacitive ultrasound transducer elements has a working surface with a diameter between 10 and 100 microns.

5. The ultrasound transducer of claim 1, wherein a furthest distance between any two of the plurality of capacitive ultrasound transducer elements is less than 1.5 mm.

6. The ultrasound transducer of claim 1, wherein the plurality of capacitive ultrasound transducer elements comprises at least 20 capacitive ultrasound transducer elements.

7. The ultrasound transducer of claim 1, wherein the plurality of capacitive ultrasound transducer elements has an average capacitance between 2.5 pF and 10.0 pF.

8. The ultrasound transducer of claim 1, wherein the ultrasound transducer is configured to be disposed within a speculum of an otoscope.

9. The ultrasound transducer of claim 1, wherein one or more of the plurality of capacitive ultrasound transducer elements has a plurality of openings in a working surface of the one or more of the plurality of capacitive ultrasound transducer elements.

10. The ultrasound transducer of claim 9, wherein the plurality of openings is arranged in a circle with a diameter of at least 10 microns.

11. The ultrasound transducer of claim 9, wherein the plurality of openings comprises at least three release holes per capacitive ultrasound transducer element.

12. The ultrasound transducer of claim 9, wherein the plurality of openings is circular in shape.

13. The ultrasound transducer of claim 9, wherein the plurality of openings is curved in shape.

14. The ultrasound transducer of claim 9, wherein the plurality of openings comprises release slits with a slit-width of a least 0.4 microns and a spring length of a least 2 microns.

15. The ultrasound transducer of claim 1, wherein the plurality of capacitive ultrasound transducer elements is arranged on the base with a hexagonal closest packing structure.

16. The ultrasound transducer of claim 1, wherein the plurality of capacitive ultrasound transducer elements is arranged on the base within a circular area with a diameter equal to an edge length.

17. The ultrasound transducer of claim 1, wherein the plurality of capacitive ultrasound transducer elements is arranged on the base within a rectangular area with a longest side equal to an edge length.

18. The ultrasound transducer of claim 1, further comprising a plurality of pads, the pads forming a plurality of electrical contact points.

19. The ultrasound transducer of claim 1, wherein the plurality of capacitive ultrasound transducer elements has an average cavity height of less than 1500 nm.

20. The ultrasound transducer of claim 1, wherein the ultrasound transducer has an 80% pull in voltage of less than 85 V.

21. The ultrasound transducer of claim 1, wherein the ultrasound transducer has a signal to noise ratio greater than 15 dB measured at a distance from 12.5 mm to 25 mm along the primary transmission axis.

22. The ultrasound transducer of claim 1, wherein the ultrasound transducer has a fractional bandwidth that exceeds 10%.

23. The ultrasound transducer of claim 1, wherein the ultrasound transducer has a projected intensity of about 10 Pa or more measured at a distance from 12.5 mm to 25 mm along the primary transmission axis.

24. The ultrasound transducer of claim 1, wherein the ultrasound transducer has a frequency bandwidth of plus or minus 25% of center frequency at full width at half maximum.

\* \* \* \* \*